(12) United States Patent
Daneshvar

(10) Patent No.: US 8,556,841 B2
(45) Date of Patent: Oct. 15, 2013

(54) DANESHVAR WRAPPING MEANS AND METHODS

(76) Inventor: Yousef Daneshvar, West Bloomfield, MI (US)

(*) Notice: Subject to any disclaimer, the term of this patent is extended or adjusted under 35 U.S.C. 154(b) by 1538 days.

(21) Appl. No.: 11/648,944

(22) Filed: Jan. 3, 2007

(65) Prior Publication Data

US 2007/0179420 A1    Aug. 2, 2007

Related U.S. Application Data

(60) Provisional application No. 60/755,269, filed on Jan. 3, 2006.

(51) Int. Cl.
*A61L 15/00* (2006.01)
*A61F 13/00* (2006.01)

(52) U.S. Cl.
USPC ............... 602/75; 602/60; 602/78; 602/79; 602/41

(58) Field of Classification Search
USPC ................ 602/41, 42, 60, 75, 78, 79
See application file for complete search history.

(56) References Cited

U.S. PATENT DOCUMENTS

| | | | | |
|---|---|---|---|---|
| 2,815,752 A * | 12/1957 | Forman | ......................... | 602/60 |
| 3,504,672 A * | 4/1970 | Moon | ............................ | 602/75 |
| 3,667,462 A * | 6/1972 | Moon | ............................ | 602/60 |
| 5,376,067 A * | 12/1994 | Daneshvar | ..................... | 602/58 |
| 5,514,155 A * | 5/1996 | Daneshvar | ..................... | 606/201 |
| 6,296,618 B1 * | 10/2001 | Gaber | .............................. | 602/75 |
| 6,398,749 B1 * | 6/2002 | Slautterback | ................... | 602/62 |
| 6,585,673 B1 * | 7/2003 | Bass | ................................. | 602/60 |
| 2003/0135146 A1 * | 7/2003 | Daneshvar | ..................... | 602/60 |
| 2003/0149389 A1 * | 8/2003 | Daneshvar | ..................... | 602/52 |

* cited by examiner

*Primary Examiner* — Victoria J Hicks

(57) ABSTRACT

This invention is related to an improved version of the wound wrapping and support means for using in a living body. Rapid wound dressing and wrapping are of significant importance and may save a lot of complications and lives. Also as important is the stability of the wrapped unit, a unit which does not stay stable on the wound will not function properly. The wound compression and prevention of bleeding are of significant importance as well as covering the whole area and preventing a site of wound to be covered. The adjustablility and being able to use one unit in more patients are of clinical and economical importance. This invention introduces a models combination of support units with straps, that can be used in various parts of the body. The new version allows the user to wrap a leg or arm easily and more securely. The use of more than one support is again stressed, so that these better unit can make the patient care a bit easier and help humanity.

9 Claims, 27 Drawing Sheets

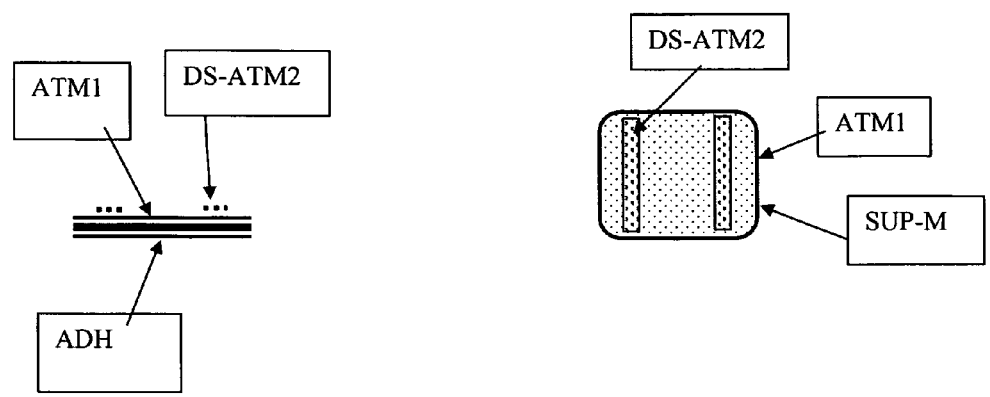
Figure 12
Figure 12A
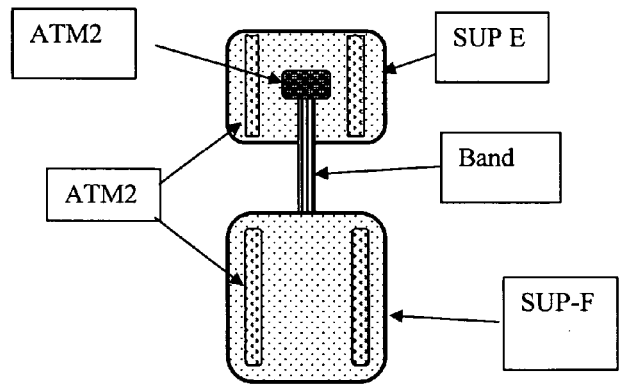
Figure 13

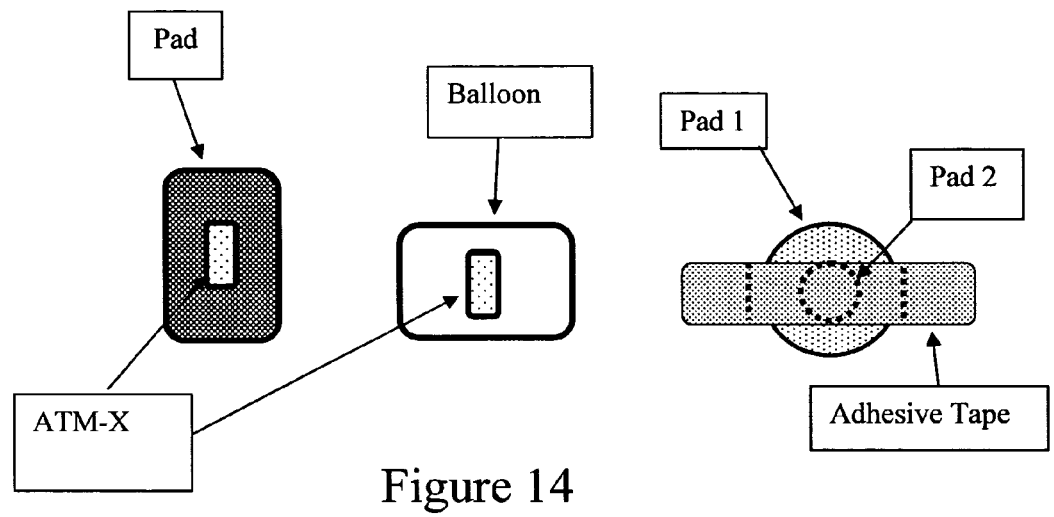
Figure 14
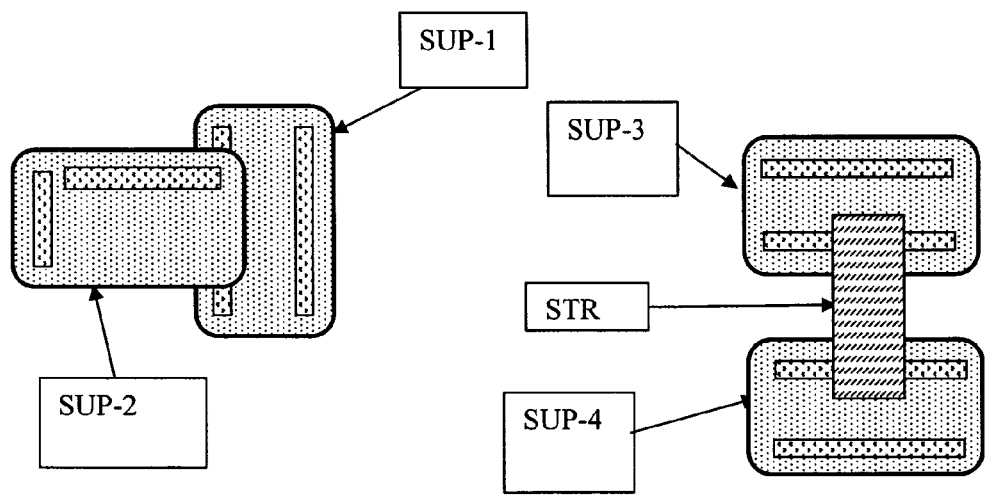
Figure 15
Figure 16

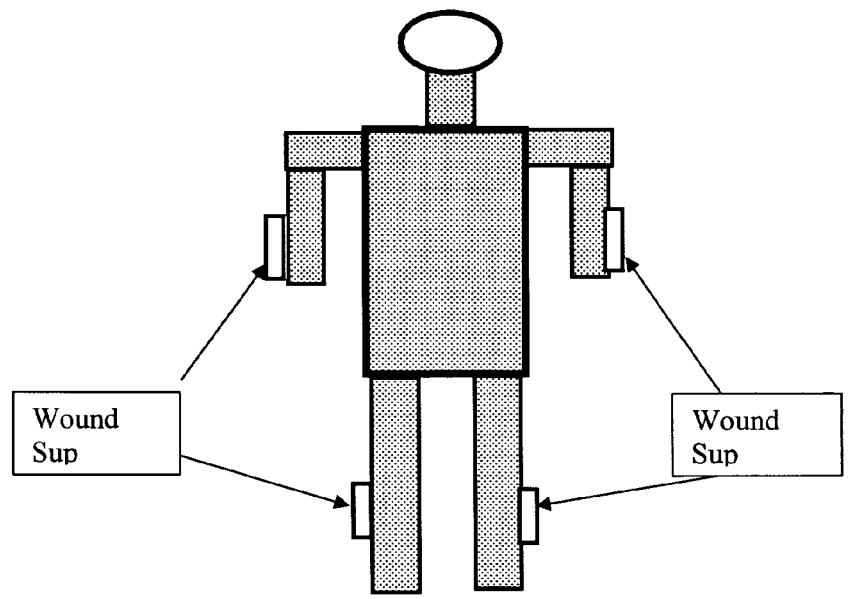
Figure 25
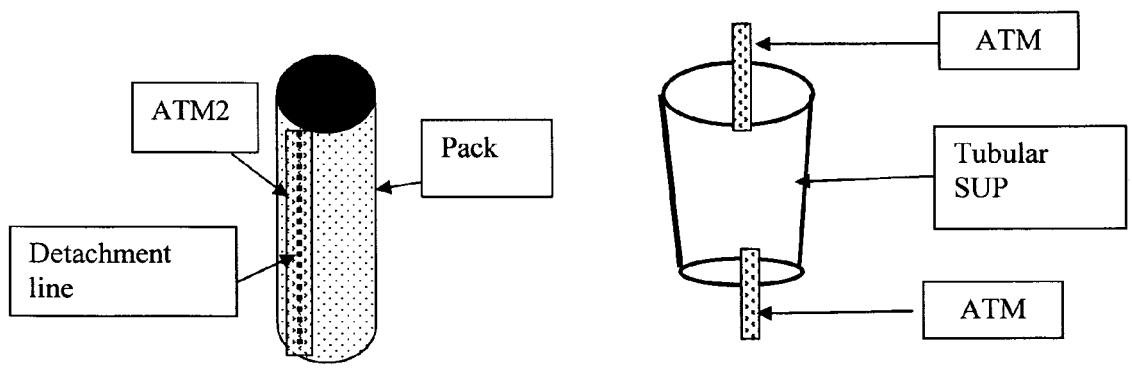
Figure 27
Figure 26

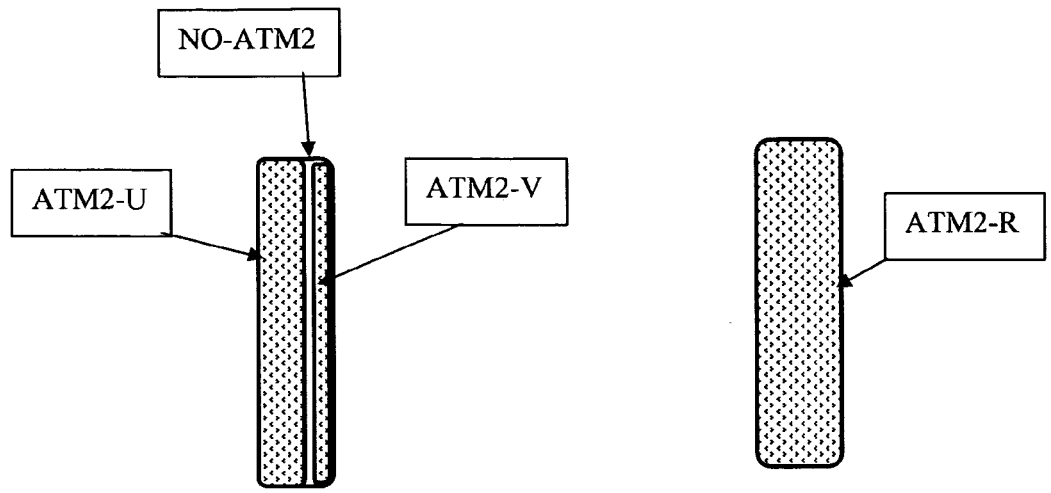
Figure 29
Figure 29A
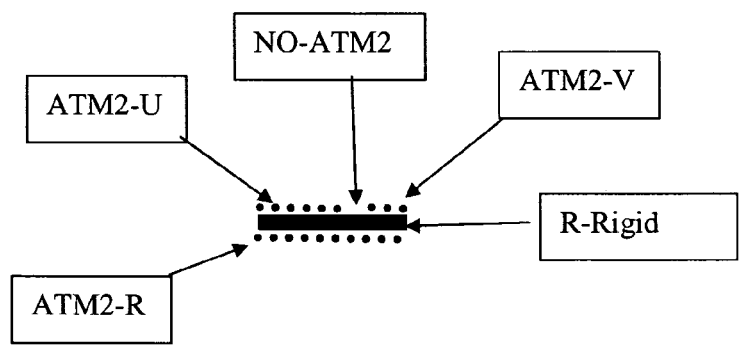
Figure 29B

DANESHVAR WRAPPING MEANS AND METHODS

This application incorporates by reference and claims the priority of the provisional application No. 60/755,269 filed on Jan. 3, 2006.

THE BACKGROUND OF THIS INVENTION

This invention is related to an improved version of the wound wrapping and support means for using in a living body. Rapid wound dressing and wrapping the wounds are of significant importance and may save a lot of complications and lives. Also the stability of the wrapped units are very important since if a unit does not stay in the intended area it will not function properly. Wound compression and prevention of the bleeding are of significant importance as well as the covering of the whole area and preventing a site of wound to be without coverage. Observing such problems in his patients the applicant decided to try to solve these problems for humans and due to his research he has introduced many models that are in the archives of the USPTO. By presenting these units the applicant wishes to help humans in a large scale.

THE BRIEF EXPLANATION OF THE INVENTION

The new methods of wound support and means of dressings that are introduced here are improved version of the models which this applicant has previously introduced to the USPTO by this applicant. These units continue to utilizes special fabrics with attachment means in its end/s as well as its body, for attaching to the support unit as well as its own body, on a detachable/re-attachable basis. This model also utilizes a support, which at least has some portion of its surface covered with a zone of attachment means such as the loop-fastener attachment means and hook fastener attachment means, it also introduces many models with use of a support means. The application also introduces wound supports means that are made from combinations of support units with straps. There is leg support which is modified and is improved with a model that covers the legs more completely and also uses extended means for providing protection to the feet and thighs. A long wrap allows the user to wrap a leg or arm easily and more securely. The use of more than one support is stressed again. The applicant utilizes his former ideas of wound supports and wound care with new ones in making more useful units for use in different areas of the body.

BRIEF EXPLANATION OF THE FIGURES

The applicant apologizes for the multiplicity of the figures and the rather difficult numbering of the figures, however, they are needed to make the models understood. He will present a colored figures, so that the examiner and the users can understand these units much better if the USPTO rules allows. He will also present a movie that shows how does these units function in real time.

Please note that some parts of this invention are shown in different figures, for preventing a crowded figures. Please also note that many of the options shown in different figures can be combined to be used in a single model.

FIG. 4AB. Shows a strap similar to the STR-F from FIG. 4 in more details.

FIG. 10A. Shows a more extensive support means for supporting the strap means from foot to the upper thigh.

FIGS. 12 and 12A. Show a support means with adhesive backing for adhering to the skin.

FIG. 13. Show a support means consisting of two supports attached to each other by a band, for use in moving area.

FIG. 14. Shows different pad means for compression of the wound for use with these units.

FIG. 15. Show two support means attached to each other.

FIG. 16. Shows two support means attached to each other with use of a strap means.

FIG. 25. Show support, strap unit attached to a garment.

FIG. 26. Shows a complimentary hose with attachment means for the leg.

FIG. 27. Show a pad means that allows quick opening.

FIGS. 29, 29A & 29B. Show an end piece for controlling the end of a strap.

DETAILED EXPLANATION OF THE FIGURES

Figure 1:
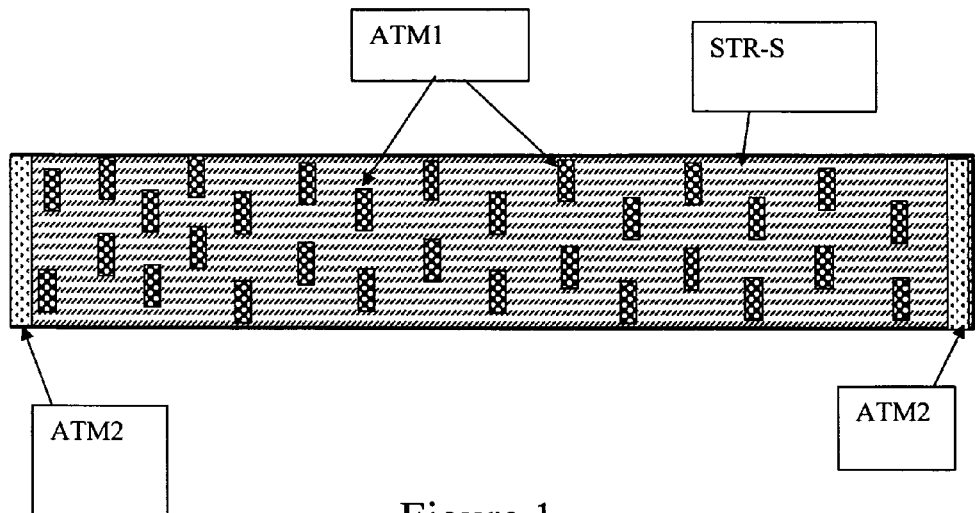
FIG. 1. Shows a strap means made from Lycra (TM) that has zones of attachment means, ATM1 on its outer surface.

FIG. 1. Shows a special strap means, STR-S made from a stretchable fabric that functions as a stretchable, loop fastener attachment means in all its length as well. Very, importantly, please note that the straps means referred in this application are made from a stretchable fabric commonly called "Lycra" (TM) and is presently available in US market. This stretchable fabric is a woven fabric that has the Lycra in it with other material such as nylon etc. In the course of his research the applicant noted that this material is capable of stretching and detachably/re-attachably, directly attaching to the support through detachable/re-attachable contact of a shiny surface of the Lycra (TM) fabric with the hook fastener attachment means, Velcro (TM). Thus he made supports with zones of the Velcro (TM) attachment means on it's outer surface. Thus the attachment means on the support comprises a suitable hook-type material, such as Velcro. The Lycra (TM) fabric has a dull (non-shiny) surface opposite the shiny surface. Because of the inventor's discovery of the properties of the Lycra, a strap made from it is both stretchable and directly attachable and detachable to the support so that attachment can be made with different degree of stretching and different distances along the length of the strap, and without any special attachment device attached to the Lycra or the strap. Thus this strap not only is a stretchable fabric but also it functions as a loop fastener attachment means in one of its surface which has a shiny appearance. Therefore, any part of this strap means in the shiny side is capable in attaching directly to a matching hook fastener attachment means, ATM2, on a detachable/re-attachable basis.

This is a very important and useful property and makes this unit unique. It allows making the units explained in this application possible.

This strap has the property of conforming to the shape of the area, that is wrapped such as a limb and joint. It allows the air to go thorough which is important in allowing the sweat to descipate and area to be comfortable. It is a thin, non irritant fabric. Importantly, the applicant has made straps by sewing or attaching this fabric with having the shiny surface to be in the outside so that both surfaces of the newly made strap allows it to be attached to the hook fastener attachment means, ATM2 on a detachable, re-attachable basis. Importantly, in this model the applicant proposes that this fabric may be further modified in order to have zones of loop fastener attachment means, ATM1 on its second/outer surface or the non-shiny surface (the shiny surface that allows the hook fastener attachment means, ATM2 to attach is mostly reffered as the rear surface). Thus it allows the end of the strap means, STR-S which has a zone of hook fastener attachment means, ATM2-B shown in FIG. 1A to be attached to those zones on a detachable, re-attachable basis. This will be similar to the fabrics that has many patches of raised flowers or special patterns etc. Importantly, such zones of loop fastener attachment means may be woven to this fabric or they may be adhered or attached to the outer surface of the LYCRA (TM) by various means. Again, the advantage of this modified strap means is that it allows the end piece of the strap, ATM2-B shown in FIG. 1A to be attached to any part of the outer surface of the strap, STR-S on a detachable, re-attachable basis. Thus it prevents the end of the strap means shown in the left side of the FIGS. 1 and 1A to be loose. This provides a grate advantage in handling the unit made from this strap for the purpose intended in this application. The advantage is that the very end of the strap after wrapping a limb will attach to the outer surface of its own and will be stable and fixed. Also in some other models it allows wrapping of the strap over itself multiple times without allowing it to slip. The support will hold the strap in position securely and prevent it from moving.

Importantly, the outer surface of the first end piece of the strap, STR-S (shown at the right side of this figure) may have a zone of loop fastener, attachment means, ATM1-A and second end of the strap means, STR-S (shown at the left side of this figure) may have a zone of loop fastener attachment means, ATM1-B. Also the first end of the strap means STR-S shown here at right side of the figure also has a zone of hook fastener, attachment means, ATM2-A on its rear surface (shown at FIG. 1A) that allows it to be attached to the outer surface of the support, SUP shown at FIGS. 4, 7 and 10 on detachable, re-attachable attachment means. The strap means may also have zones of adhesive means on its rear surface to allow the strap to be adhered to the skin or to the underlying strap or other objects in order to add more stability and security as shown at ADH, in FIG. 1A.

Figure 1A:
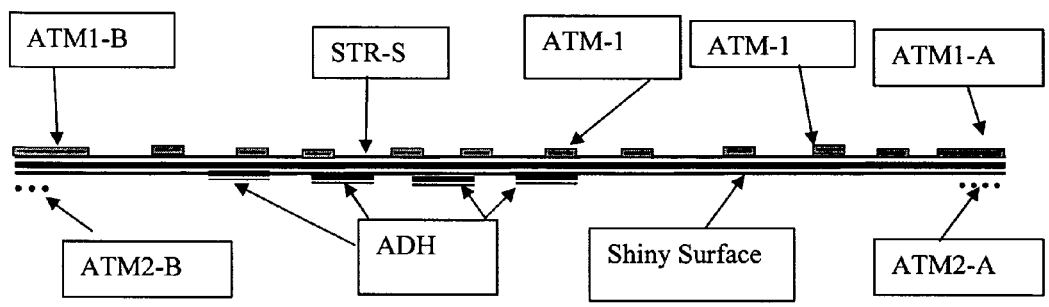
FIG. 1A. Shows the cross cut view of the a strap means shown at previous FIG. 1.

FIG. 1A. Shows schematically the cross cut side view of the strap means, STR-S shown in previous figure. In this figure the body of the strap means is shown at STR-S, the shiny face of this strap means is in the lower side and the upper surface of this strap has zones of the loop fastener, attachment means, ATM1 on it only few are marked. Both ends of this strap means have a zone of loop fastener, attachment means, ATM1-A and ATM1-B on its upper/outer surfaces respectively and a zone of the hook fastener attachment means, ATM2-A and ATM2-B respectively. Importantly, this method allows the end of the strap itself or the beginning of another similar strap to be attached to this strap means on a detachable, re-attachable attachment basis, in order to extend the strap means and control the end of the final strap means or to lengthen the strap means.

Importantly, the strap may also have zones of adhesive means, ADH, that allows the strap to be adhered to the skin or to the underlying strap or other objects in order to add more stability and security.

Figure 1B:
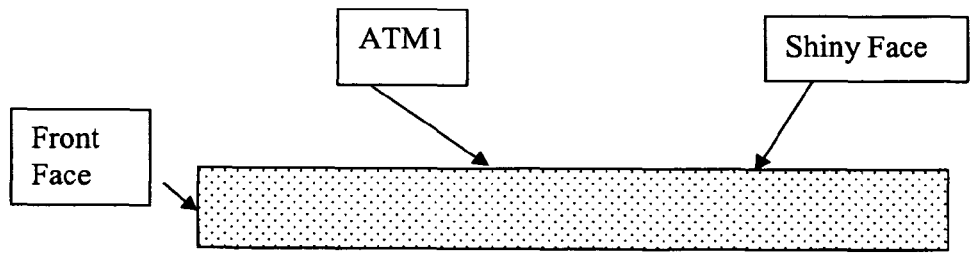
FIG. 1B. Shows the front view of a stretchable strap means, that its both surfaces function as a loop fastener attachment means.

FIG. 1B. Shows the front view of a stretchable strap means, made from a fabric that both of its surfaces; in front and in rear functions as a stretchable, loop fastener attachment means, ATM1, which is capable of attaching to the hook fastener attachment means, ATM2 directly, on a detachable/re-attachable basis. The front face, is shiny face, is marked at Shiny Face.

Figure 1C:
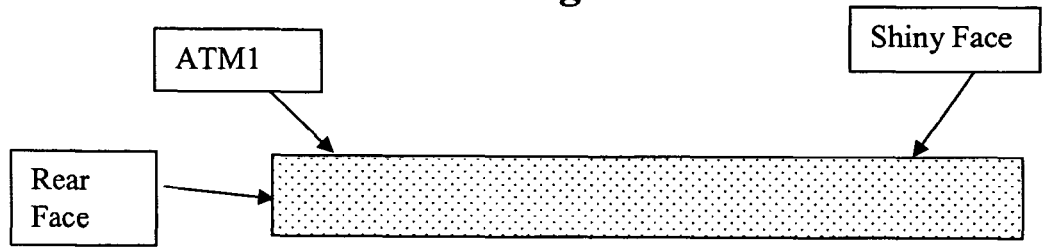
FIG. 1C. Shows the rear view of a the stretchable strap means, shown in previous FIG. 1B.

FIG. 1C. Shows the rear view of a the stretchable strap means, shown in previous FIG. 1B. In this view the rear face, Rear Face is also a shiny face, marked at Shiny Face and functions as the ATM1.

Figure 1D:
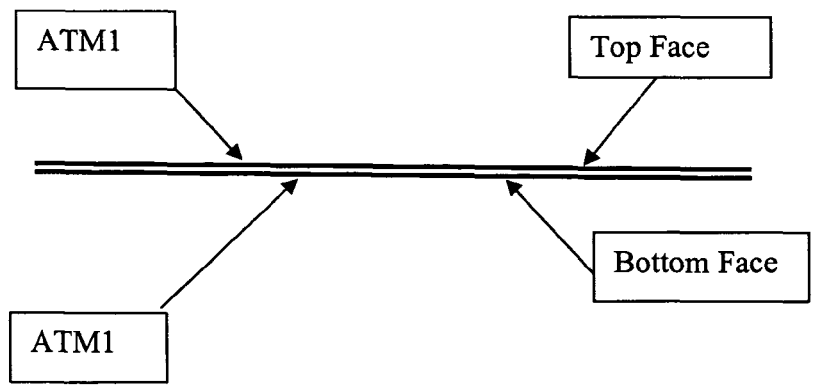
FIG. 1D. Shows the cross cut view of the strap means, shown at previous FIGS. 1B and 1C.

FIG. 1D. Shows the cross cut view of the strap means, shown at previous FIGS. 1B and 1C which shows that both the top and the bottom surfaces of this fabric are capable of functioning as a stretchable, loop fastener attachment means, ATM1 and are capable of attaching directly, to the hook fastener attachment means, ATM2 on a detachable/re-attachable basis.

Figure 2:
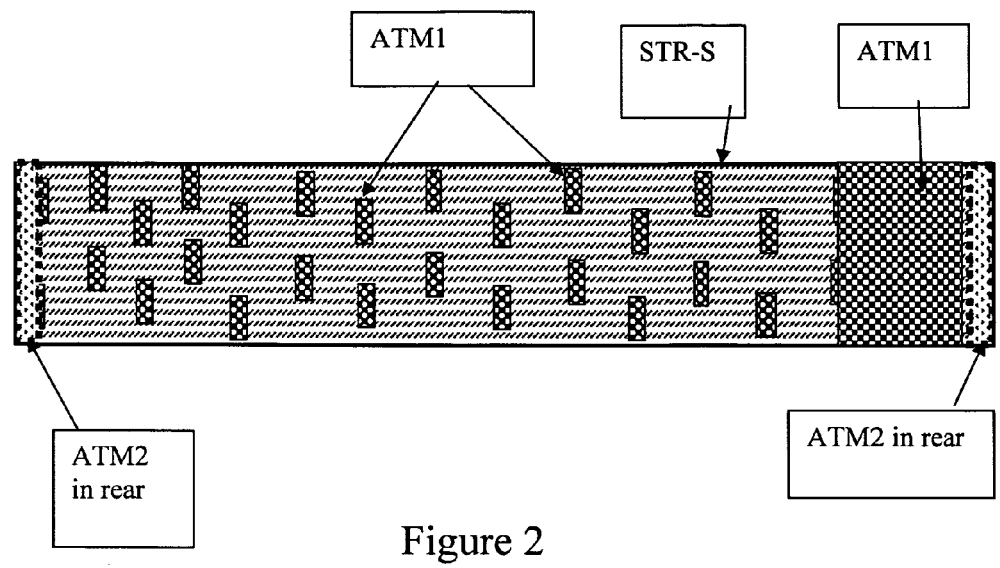
FIG. 2. Shows a strap means that has small and large zones of loop fastener attachment means, ATM1 on its surface.

FIG. 2. Shows a strap means similar to the model shown at previous FIG. 1 except in this model the strap means, STR-S, also has rather large zone of loop fastener attachment means, ATM1 on its surface, shown in the right side. So that this allows the end of a similar strap which has a zone of hook fastener attachment means, ATM2 on it's rear surface to be attached to this zone on a detachable, re-attachable attachment basis, after it is wrapped around the limb and attached to the support, SUP. This provides significant advantage in some models of these units and prevents from the free end of strap to be loose. This is useful when the length of the strap is longer and will exceed the width of the support and needs to be controlled.

Figure 2A:
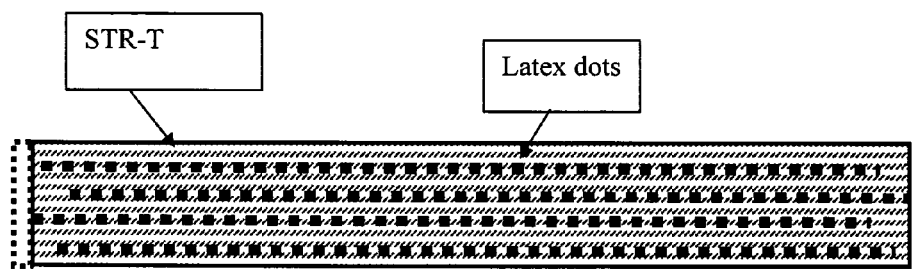
FIG. 2A. Shows a strap means that has dots of latex or rubbery type material on it to prevent from skidding.

FIG. 2A. Shows a strap means made from Lycra (TM) except the body of this strap means, STR-T, has dots or zones, Latex dots of a material such as latex, rubbery, or other synthetic material that are raised or have raised parts that will function for preventing the overlaping strap to skid. These raised zones can be located on the one surface of strap and it will provide a sort of grip on the in-coming surface of the strap mean or the fabric so that the combination will prevent them from sliding, or displacement easily. Importantly, these dots or zones can be only in one side or in both sides of this fabric.

This method is designed to provide the following advantages.
1. More stability to these units. So that one unit would not slide or skid over the other and will keep its position as it was placed initially.
2. It will not stick these straps to each other.
3. It may promote the attachment of these two straps.

In this figure this material is shown in the form of dots, Latex dots which is scattered all over, although they may be made in the form of lines of different shapes or patches. The thickness and the shape of these spots or means may wary and they may have a shape that will engage with each other when are in approximation or the contact of each other.

Figure 3:
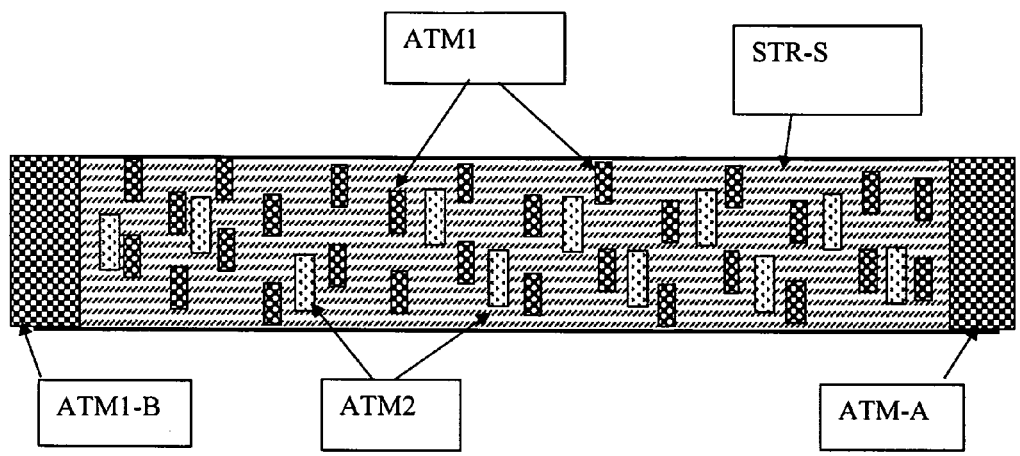
FIG. 3. Shows a strap means similar to FIG. 1 except the strap means, STR-S, also has zones of hook fastener attachment means ATM2 on it's outer surface.

FIG. 3. Shows a strap means similar to the model shown at previous FIG. 1 except in this model the strap means, STR-S, also has zones of hook fastener attachment means, ATM2, on it's outer surface. So that this modification allows the shiny, rear surface of the body of the strap, made from a stretchable, loop fastener attachment means to be attached to such zones of ATM2 on a detachable, re-attachable attachment basis. This provides significant advantage and causes.
1. More stability of the unit and prevents the outer strap to slide from the inner strap when the strap is wrapped on a patient's limb.
2. Allows the rear surface of the strap to be attached to these zones when it does not have ATM2 zone on it.
3. Allows other strap to be attached to the first strap on a detachable, re-attachable attachment basis.

Figure 3A:
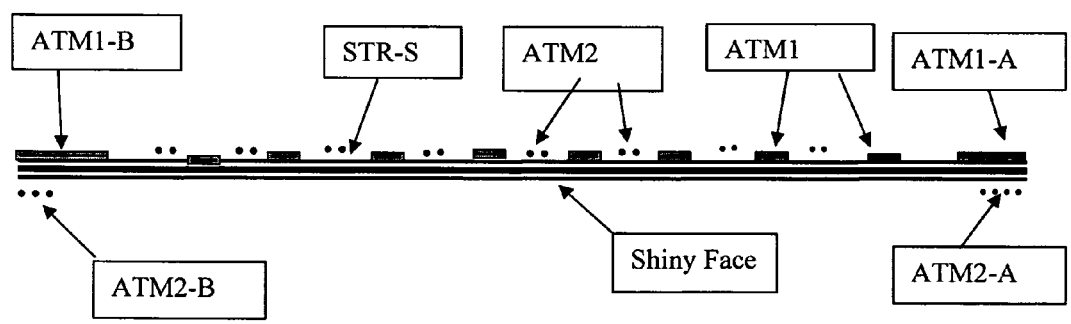
FIG. 3A. Shows the cross cut side view of the strap means, STR-S shown in previous FIG. 3.

FIG. 3A. Shows schematically the cross cut side view of the strap means, STR-S shown in previous FIG. 3. In this figure the body of the strap means is shown at STR-S, the shiny face, Shiny Face of this strap means is in the lower/rear side and the upper surface of this strap has zones of both the loop fastener, attachment means, ATM1 and also hook fastener attachment means, ATM2 on it only few are marked. Importantly, this allows the end of the strap means, STR-S to attach to the loop fastener attachment means, ATM1 of the outer, surface of this strap when is wrapped on a living body, also the inner/shiny surface of the strap means, STR-S to attach to the zones of the hook fastener attachment means, ATM2 of this strap on a detachable, re-attachable attachment basis, for making a very sturdy, stable attachment.

Both ends of this strap means have a zone of loop fastener, attachment means, ATM1-A and ATM1-B on its upper/outer surfaces respectively and a zone of the hook fastener attachment means, ATM2-A and ATM2-B respectively.

Figure 4:
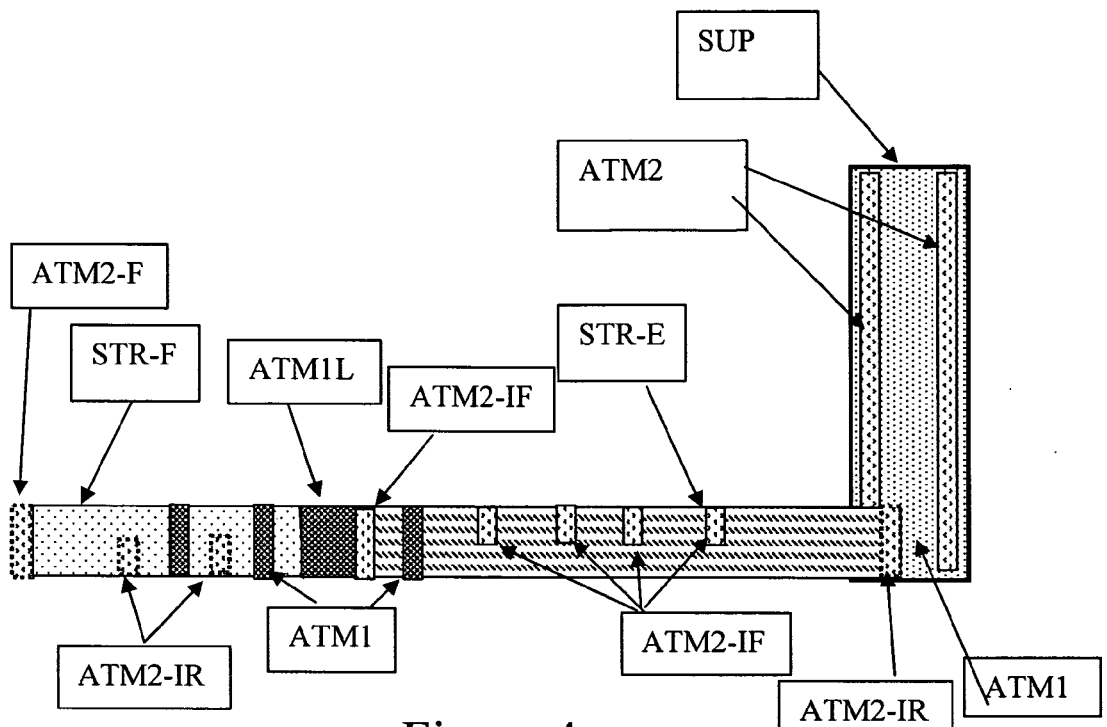
FIG. 4. Shows a support with a long strap means for being wrapped around a limb.

FIG. 4. This figure shows a very distinct wrapping system of a limb and a method of doing it which consist of a support, strap means similar to the main models discussed in the text, except in this model the unit has.
1. A support means, SUP which is made from a long layer of either laminate or similar unit which has an outer cover made from loop fastener attachment means, ATM1 marked in the bottom of the support. Which also has zones of hook fastener attachment means, ATM2 on it. Thus it allows the shiny surface of a strap means, STR made from a material explained in the test such as lycra to be attached to the zones of ATM2 located at the surface of the support, SUP on a detachable, re-attachable attachment basis. Also the end piece of the strap means, with ATM2 (in this figure specified as ATM2-IR) to be attached to the surface of the support means, SUP on detachable, re-attachable basis. The long zones of the hook fastener attachment means on the surface of the support, SUP can be
1. From soft flexible material.
2. From a hook fastener attachment means with a body made of a rather rigid material in order to prevent the support means, SUP from shrinking and bending.
3. From combinations of multiple small pieces that can be removed and re-attached.
4. Can be double sided hook fastener attachment means. Which can be attached to the surface of the support, SUP.

Importantly, in this model the body of the strap means, STR consist of two segments.
a. The initial first segment, STR-E which is attached to the support, SUP, is a long elastic strap means, which the shiny surface of the strap is in the rear/lower side of it. So that this part will wrap around the limb and attach to the zones of the ATM2 of the support, SUP on a detachable, re-attachable attachment basis. Importantly, the STR-E may have zones of hook fastener attachment means, in its front surface, ATM2-IF which allow the shiny surface of the strap means, STR-E to attach to these zone after the first wrap around the limb. Importantly, this figure such zones may be located only in the upper border of the strap, STR-E in order to prevent them from being exposed (without being covered) and to attach to the dress of the users. Since the strap will be moving up from the ankle toward the knee.
b. The later, second segment, STR-F is also made from a material such as lycra but its shiny surface is located in the outside/in front so that the incoming end piece with ATM2-F, will attach to it on a detachable, re-attachable basis. Importantly, the rear surface, dull surface of the segment STR-F may have zones of hook fastener attachment means, ATM2-IR in order to allow the upcoming part of this strap to be attached to such zones on a detachable, re-attachable attachment basis. Importantly, as shown in this figure, such zones may be located only in the lower border of the strap, STR-E in order to prevent them from being exposed (without being covered) and to attach to the dress of the users. Since the strap will be moving horizontally or somewhat down from the knee toward the knee.

Importantly, this strap means is long for being long enough to be wrapped around the leg, arm or another part of the body and to have its end piece, ATM2-F to be attached to it by attachment means, ATM2 or any other means on a detachable, re-attachable attachment basis, by one of following means.

1. Having zones of attachment means such as loop fastener attachment means, ATM1, on the outer surface of the strap means so that the end piece of the strap which has attachment means to be attached to it on a detachable, re-attachable attachment basis. An example of this is shown at zones of ATM1 at the outer surface of the end of the STR-E and also at the outer surface of the strap, STR-F. These zones allows the hook fastener attachment means, ATM2-F from the end of the strap STR-F to attach to one of these, which ever zone that the end piece matches its position and on a detachable, re-attachable attachment basis and in a more durable basis.
2. Having a strap means made from double sided lycra, so that the hook attachment means on the body of the strap or at the end piece of the strap, ATM2-F to be attached to it on a detachable, re-attachable attachment basis.
3. Having one segment of the strap, STR-E such as the initial part of the strap to have an outer surface of the lycra that has a shiny surface and allows the end piece of the strap, ATM2-F to be attached to it on a detachable, re-attachable basis.
4. The rest of the strap may have a segment such as STR-F which has an outer surface made from shinny surface of lycra or double sided lycra that allows any part with ATM2 on it or the end piece ATM2-F to attach to it on a detachable, re-attachable basis.
5. Use of a complementary piece such as one shown at FIG. 4A.
6. Use of various snaps mean, some shown at this application at FIGS. 19, 20 and 21.

The optional segment of the loop fastener attachment means, ATM1, such as the shiny surface on the initial outer surface of the strap STR-E can play a very crucial role in allowing the end, ATM2-F of the strap means, STR-F to be attached to it on a detachable, re-attachable attachment basis. Since the straps can be attached to different spots of this piece thus this allows the functional length of this segment to be decided so that the end ATM2-F will fit and attach to this segment and allow multiple detachment and re-attachment to occur. Also it allows custom made units to be made for this purpose so that the end of the strap, ATM2-F will end to attach to this segment.

Also the zone of hook fastener attachment means, ATM2 on the ATM1 allows the body of the STR-F to be partially attached to it for some stability. The method of use.

In this method the user places the support means, SUP on the leg or arm in a suitable place and the strap can be attached to the support means, SUP on one end of the SUP or the other end. For example the support-strap means, will be placed in lower leg close to the ankle and the user will wrap the strap around the leg obliquely, moving up close to knee while pulling. In each wrapping circle the inner surface of the strap will attach to the ATM2 of the SUP till the STR-F comes and the end of this segment, ATM2-F will attach to the outer surface of the STR-F on a detachable, re-attachable basis.

The end of the strap, STR-F shown at ATM2-F is made of hook fastener attachment means or similar unit has capability to attach to the outer surface of the strap on detachable, re-attachable basis.

The end piece of the strap, STR-F has an attachment means, ATM2-F which can be also as follows.
1. The rear surface of this attachment means to be, hook fastener attachment means, ATM2. And the front also to have a the same.
2. The rear surface of this attachment means to be the hook fastener attachment means, ATM2. And the front to have a loop fastener attachment means, ATM1.
3. In some case the unit shown at FIG. 4A will be utilized for controlling the end of the strap means. In such case the complimentary piece, SUP-B, shown at FIG. 4A will be attached to the end of the ATM2-F. Then the strap, STR-G will be wrapped to allow its end piece, ATM2-G to attach to the SUP-B. The D-ring of this unit allows the length of the STR-G to be adjusted, so that the total length of this piece will be proper.

Figure 22:
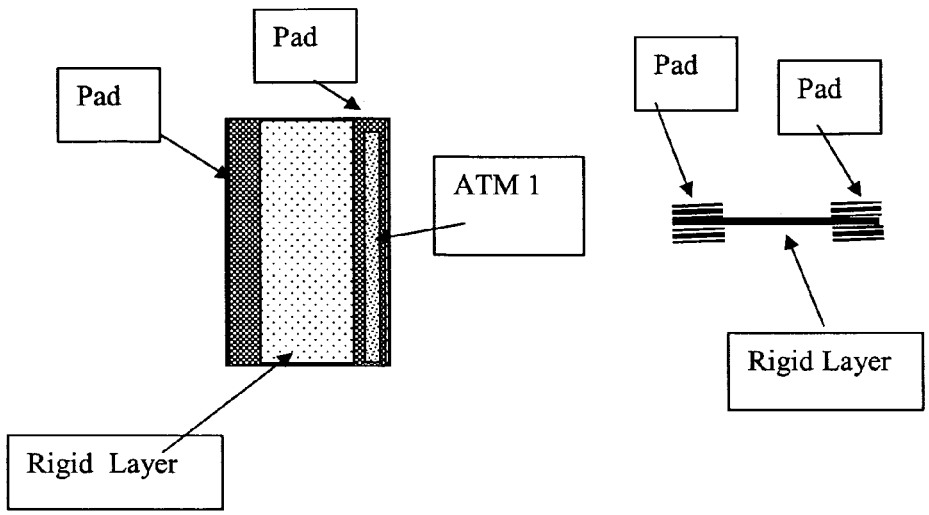
FIG. 22. Show a flat tool designed to allow easy application of a long strap.
Figure 23:
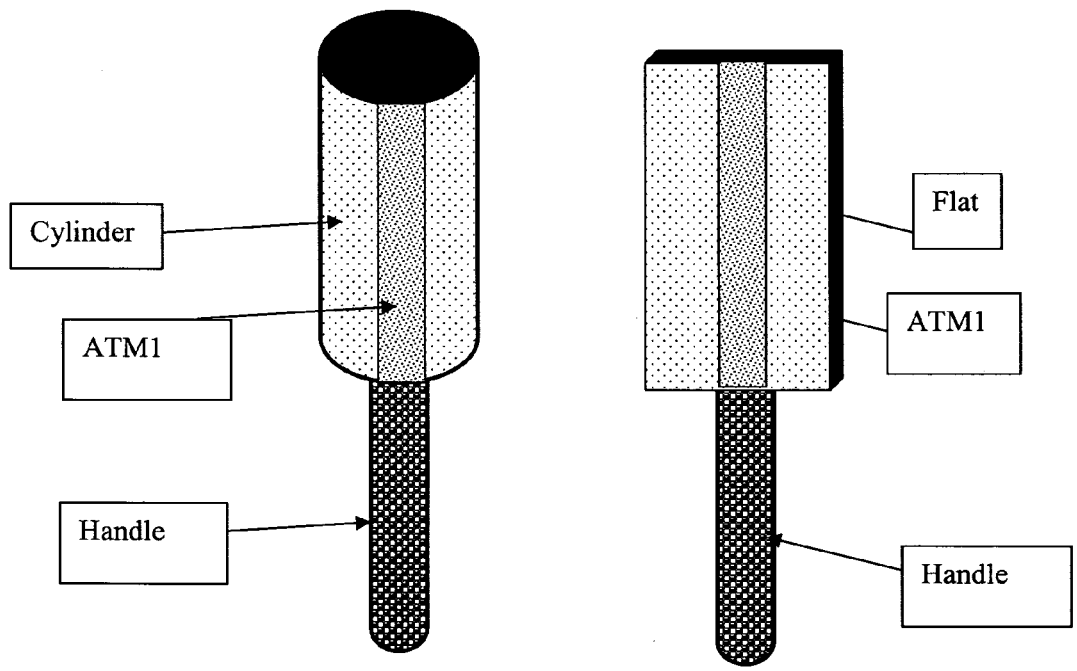
FIG. 23. Shows a method and the tool for easy application and the removal of a long strap.

Importantly, the strap means may use an adaptor that allows the strap to be delivered easily and also to be removed and re-applied easily. This adaptor is shown at FIGS. 22 and 23.

Figure 4A:
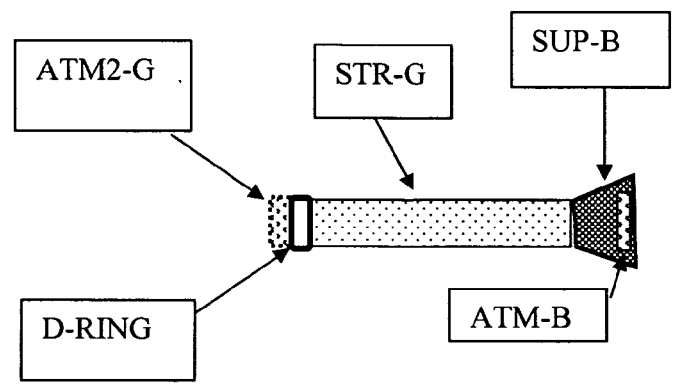
FIG. 4A. Shows an extension piece for the unit shown at previous FIG. 4.
Figure 4A:
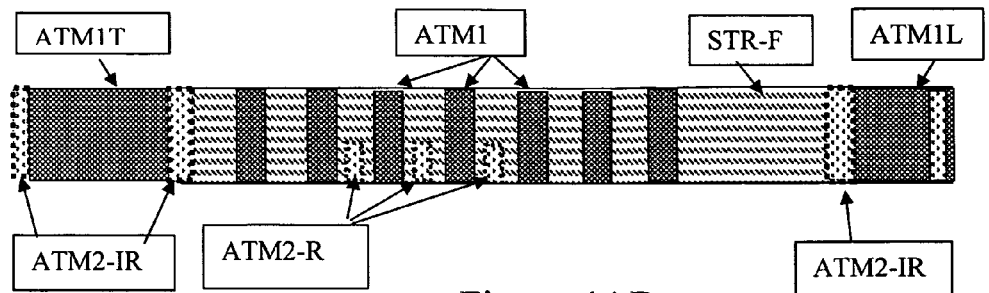
Figure 4B:
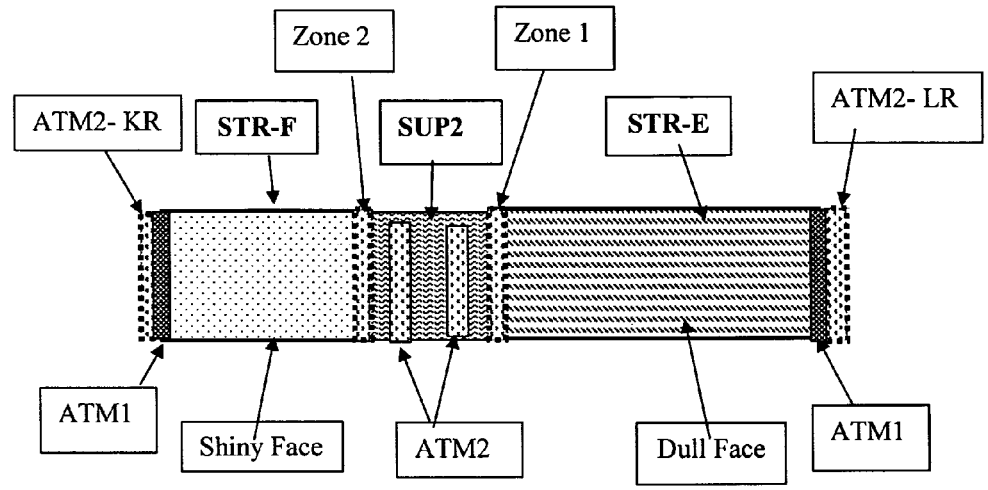
FIG. 4B. Shows a complimentary unit for the unit shown at previous FIG. 4.
Figure 4C:
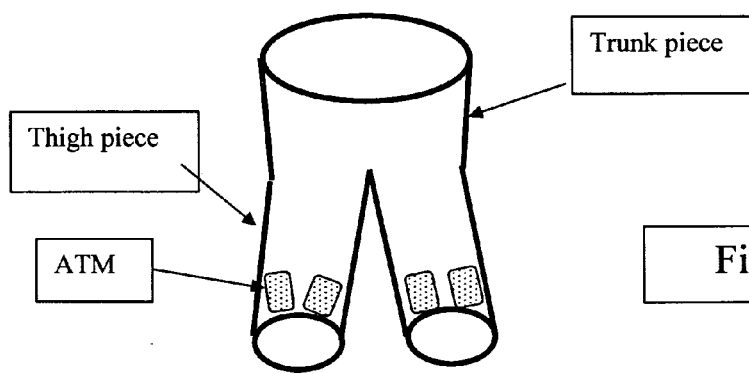
FIG. 4C. Shows a hose means that allows the strap-support means to be attached to it.
Figures 4D, 4E, 4F:
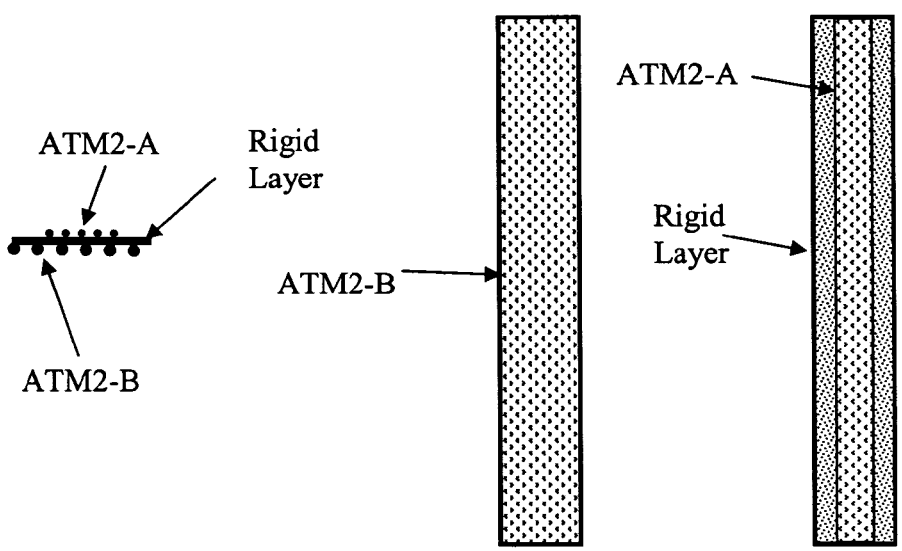
FIG. 4D, shows double sided attachment means, ATM2 with a rigid body for attachment to the front surface of the support.
FIG. 4E, shows the rear surface of the unit shown at FIG. 4D.
FIG. 4F, shows the cross cut view of the unit shown at FIGS. 4D and 4F.

Importantly, the zones of hook fastener attachment means, ATM2 located on the support, SUP may be made by following the following methods, shown at FIGS. 4D, 4E and 4F.
1. A rather rigid layer shown at Rigid Layer at FIG. 4D which has an outer layer with
   A. a zone of hook fastener attachment means, ATM2-B shown at FIGS. 4E and 4F on its rear/lower so that it can be attached to the outer surface of the support when the outer surface of the support has the property of the loop fastener attachment means on its surface.
   B. A zone of hook fastener attachment means, ATM2-A on its front/outer surface, shown at FIGS. 4D and 4F. so that the incoming strap means, STR can be attached to it on a detachable, re-attachable attachment basis.

Importantly, the grip of these two hook fastener attachment means may vary to allow more grip for attaching to the support, SUP so that when the strap, STR is being pulled away this piece would not be dislodged.

What happens is that since the lower surface of the DS-ATM2 has more surface covered with is piece shown at those figures at ATM2-B and also has more grip as it is chosen to, the strap will detach from the ATM2-A of these units without causing the rigid piece to detach from the support.

Importantly, the body of the rigid layer will prevent the support from shrinking.

The use of hand hold tools with these units.

The applicant has designed a hand hold device shown at FIGS. 22 and 23 for use with the unit shown in this figure and related items. The use of this hand hold device/adaptor is that it allows the strap to be applied/wrapped on the limb and removed from the limb with significant ease. This hand hold device may have different versions.

1. In one version the shown in FIG. 22 the device consist of a rectangular shaped, rigid layer, Rigid Layer with a zone of loop fastener attachment means, ATM1 on it. Pieces of pads, Pad are wrapped in the sides of this unit to provide more body and grip to this unit. The zone of loop fastener attachment means, ATM1 may be on one or more of these pads or the body of pad may be made with an outer surface made of loop fastener attachment means, ATM1. This zone allows the end of the strap means STR-F from FIG. 4 which has a zone of ATM2 to be attached to it on detachable, re-attachable attachment basis and to be wrapped around it.

At the time of storage the first free end of the strap, STR-F which has a zone of ATM2 will be attached to the body of this device and the strap will be wrapped around the device and will be hold in a compact secure condition. At the time of delivery the second or the free end of strap will be attached to the body of the support, SUP and the strap will be unwraped from this unit and wrapped around the limb till finally it's end piece will be attached to the outer surface of the strap means.

In second model shown at FIG. 23 the hand held unit has a cylindrical, or cuboid shape body, Cylinder or Cuboid piece with a handle, Handle. The outer surface of the body of this piece has a zone of loop fastener attachment means, ATM1 on it. Again this zone allows the end of the strap means STR-F from the FIG. 4 which has a zone of ATM2 be attached to it on a detachable, re-attachable basis. At the time of storage the first free end of the strap, STR-F which has ATM2 will be attached to the body of the adaptor and the strap will be wrapped around the adaptor and will be hold in a compact, controlled fashion. At the time of delivery the second or the free end of strap will be attached to the body of the support, SUP and the strap will be unwraped from the adaptor and wrapped around the limb, till finally its end piece will be attached to the outer surface of the strap means. Importantly, the handle may be made to move and hide inside the body of this unit.

Importantly, the support means of this unit can be modified in order to extend from leg to the waist area in order to allow the strap means to move up and cover from the feet to the upper thigh area. One example of this method is shown at FIG. 4. In this model the body of the support means will be modified to be long with joints. The outer surface of the support means will be made from loop fastener attachment means, ATM1 to allow hook fastener attachment means, ATM2 to attach to it. Also it will have zones of hook fastener attachment means, ATM2 (not shown in that figure), in order to allow the strap to wrap around it and be held in place securely. The unit can be modified for use with multiple straps as well.

FIG. 4A. This figure shows a complimentary support, strap means, which is similar to the units shown in previous figures except.
1. The support means shown at SUP-B may have different shape such as trapezoid shape in order to transform the strap, STR-F from the previous unit to a narrower strap means, STR-G. The end of the, STR-G has ATM2-G on its rear surface of the end. This strap means also may use an optional D-ring, D-RING to allow the length of the strap, STR-G to be adjusted and this end to be attached to the outer surface of the support, SUP-B after it wraps around the limb on a detachable, re-attachable basis.
2. Hook fastener attachment means, ATM2-B on the support allows the body of the strap to attach to them partially and be reasonably stable. This method allows the end of the strap means STR-F to be controlled easily.

FIG. 4AB. Shows schematically, a strap means similar to the STR-F which has a stretchable body made from Lycra (TM) that has two ends with zones of hook fastener attachment means, ATM2-IR at the rear surface of these ends at each side. So that these end pieces allows attachment of the ends of this strap means to the outer surface of two long zones of loop fastener attachment means, ATM1L, ATM1T on a detachable re-attachable basis. This allows the point of the attachment of the strap, STR-F to the zones of ATM1L and ATM1T to be decided in order to change the effective length of the ultimate piece. Thus by this method the final end of the strap means at the left side of the figure will be able to wrap around the limb and to come back and attach to the zone of ATM1 on a detachable, re-attachable basis. This strap also has multiple zones of loop fastener attachment means, ATM1 on the outer surface so that the end piece of the strap, which has a zone of hook fastener attachment means, ATM2-IR in its rear surface to be able to attache to it on a detachable, re-attachable basis. Also of interest is the presence of hook fastener attachment means, ATM2-R in the rear surface of this strap, that allows these zone to attach to the outer surface of the underlying surface of this strap on a detachable, re-attachable means.

FIG. 4B, shows the more details of the strap means, shown at FIG. 4AB. In this model a piece of support means, SUP which has an outer layer covered from loop fastener attachment means, ATM1 has a body to function as a zone of attachment means that allows the following.
1. A first strap, STR-E to be attached to another strap, second strap STR-F by use of a second support means, SUP2 on a detachable, re-attachable means. Please note that these strap support means will be used with a long first support means, SUP shown at previous FIG. 4 not shown here.
2. The support2, SUP2 to allow the first strap, to attach to its attachment means, ATM2 after being wrapped on the limb.
3. To allow the length of the straps to be modified.
4. Allows the functional property of the outer sides of the strap means to be changed. Dull face in front of the first strap means, STR-E and shiny face in front of the second strap means, STR-F.

In this view the support, SUP2 is attached to the strap, STR-E that the front face of the lycra, Dull Face on a detachable, re-attachable attachment basis, in zone 1. In the left side it is attached to the second strap, STR-F made from Lycra shiny face in front, Shiny Face at zone 2, Zone 2 on detachable, re-attachable basis. The strap means, STR-E and STR-F have hook fastener attachment means, ATM2-LR and ATM2-KR on the rear surface of their ends respectively. Importantly, the front end of these strap means may also have loop fastener attachment means, ATM1 on their outer/front surface to allow one end of another strap to be attached to it. Importantly, the size, shape and nature of the second strap means may vary.

FIG. 4C. Shows symbolically a method of combining the strap-support means shown in FIG. 4 with other units for the purpose of making a complete system to cover from the foot to the thigh area. In this method the user wears a stretchable panty hose system shown in this figure which is designed to have the capacity of compression of the thigh area, it can also extend to go over the knee area and to have the coverage of the knee as well, even may extend to the leg and foot. This system has attachment means, ATM designed to accept the support of the unit shown at FIG. 4. So that the combination will have the more adjustable compression of the legs which are more important due to the severity of the vascular problems and the higher hydrostatic pressure in the area. AS well as the compression of the thigh and knee area. In this figure the trunk piece of this unit, Trunk piece is shown as well as the pieces for the thigh, Thigh piece with the attachment means, ATM shown.

Importantly, the unit may consist only from the leg support and the knee hose as shown at FIG. 26.

FIGS. 4D, 4E and 4F shows a method which importantly, the zones of hook fastener attachment means, ATM2 located on the support, SUP may be made by use of a unit that has.
1. A rather rigid layer shown at Rigid Layer at FIG. 4D which has an outer layer with
   A. a zone of hook fastener attachment means, ATM2-B shown at FIGS. 4E and 4F on its rear/lower so that it can be attached to the outer surface of the support when the outer surface of the support has the property of the loop fastener attachment means on its surface.

B. A zone of hook fastener attachment means, ATM2-A on its front/outer surface, shown at FIGS. 4D and 4F. so that the incoming strap means, STR can be attached to it on a detachable, re-attachable attachment basis.

Importantly, the grip of these two hook fastener attachment means may vary to allow more grip for attaching to the support, SUP so that when the strap, STR is being pulled away this piece would not be dislodged.

Importantly, the body of the rigid layer will prevent the support from shrinking.

FIG. 4D, shows the front surface of this unit. Which shows the body of the rigid layer, Rigid Layer with a zone of hook fastener attachment means, ATM2-A located on it.

FIG. 4E, shows the rear surface of the rigid layer. Which is covered with the hook fastener attachment means, ATM2-B.

FIG. 4F, shows the cross cut view of the unit shown at FIGS. 4D and 4E. This view shows the body of the rigid layer, Rigid Layer with a zone of hook fastener attachment means, ATM2-A located on it's top and a lower surface which is fully which is covered with the hook fastener attachment means, ATM2-B.

Figure 5:
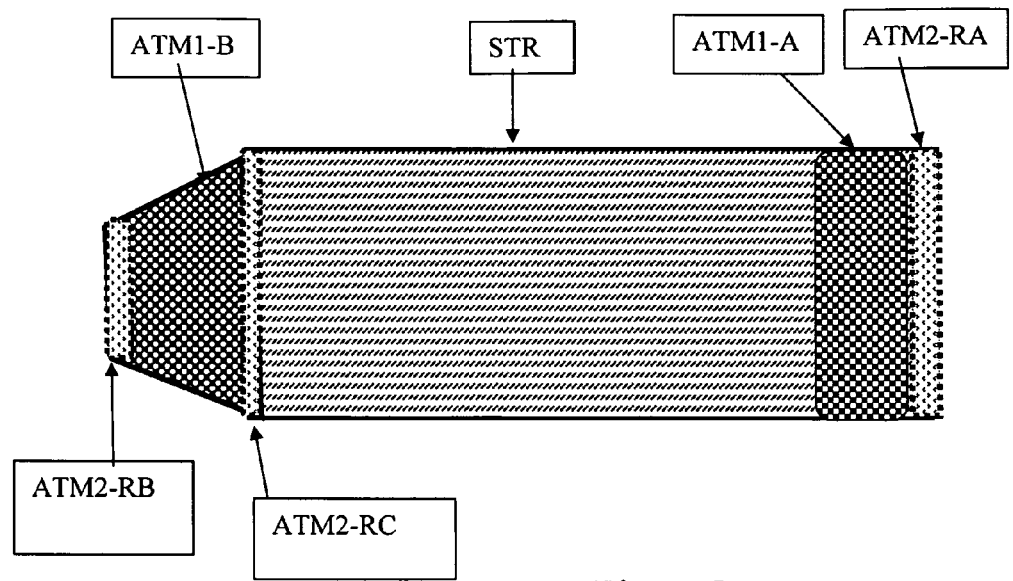
FIG. 5. Shows a strap means with trapezoid detachable, re-attachable end means.

FIG. 5. Shows a strap means that has a wide body but with smaller end pieces that allows the hand of humans to grip the end of a wide strap and to apply it easily. This design is due to the size of the hands of the humans which many have a rather smaller hands and it will be difficult for the hand of the humans to hold the end of a wide strap and pull it for attachment to the support properly. Thus a transitional piece, ATM1-B allows the end of the wide strap to be attached to an smaller end piece, ATM2-RB that is easy for being held.

This strap, STR is made from a stretchable material which is explained in the text such as lycra and has a wide rectangular shape designed to overlap the other straps when they are placed on a support means such as one shown at FIG. 4. So that the combination of these strap means with support will cover a long area such as a leg without leaving a part of the leg without coverage. This strap means consists of a wide strap made from stretchable material such as lycra that has a hook fastener attachment means, ATM2 at the rear surface of it's end shown at ATM2-RA, that allows it to attach to the support, SUP (not shown in this figure but it will be similar to the support shown at FIG. 4) on a detachable, re-attachable basis. This strap has a rather wide zone of loop fastener attachment means, ATM1-A, on its outer/rear surface that allows the end of the strap ATM-RB to attach to it, after being wrapped over the support, SUP and if the strap was long enough so that such attachment was needed. In this model the end piece of the strap, shown at ATM1-B has a rather trapezoid end means that can be also attached to the strap means on a detachable, re-attachable basis. This allows the wide end of the strap to be attached to a smaller end piece ATM1-B so that the hand of the users can hold it. This method is particularly useful when two or more straps are to be used in order to cover a part such as the leg and to have the straps to overlap each other for preventing from gaps between the straps. The part ATM1-B allows the end of the other straps which has hook fastener attachment means, ATM2 to be attached to it on detachable, re-attachable basis.

The end of the strap, STR has a zone of hook fastener attachment means, ATM2-RC that allows it to be attached to the longer side of a trapezoid loop fastener attachment means, ATM1-B on its outer surface. The ATM2-RB allows this end to attach to the support, SUP or the loop fastener attachment means, ATM1-A of this strap on a detachable, re-attachable basis. This method allows two or more strap to be used in order to cover the leg and to have the straps to overlap each other for preventing from gaps between the straps. Similar to the unit shown at FIG. 7.

Figure 5A:
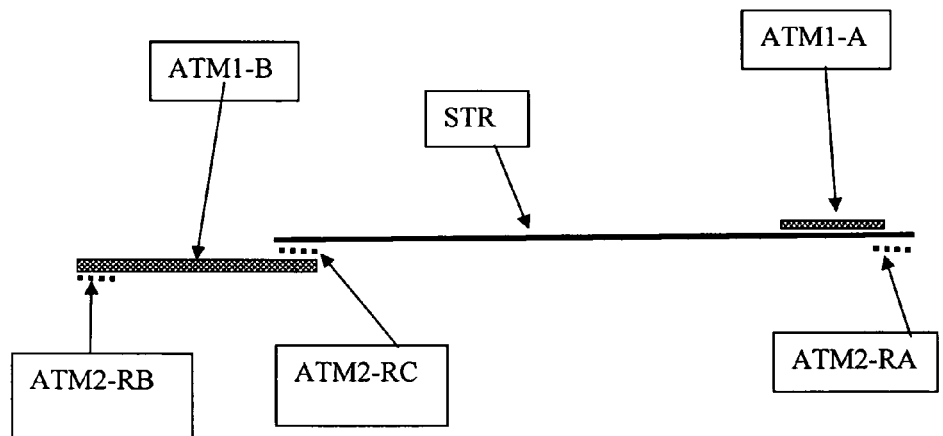
FIG. 5A. Shows the cross cut side view of the strap means, shown in previous FIG. 5.

FIG. 5A. Shows the cross cut view of the unit shown at FIG. 5. In this view the strap is shown at STR, the hook fastener attachment means ATM2-RA is in its lower surface, shown at right side of the figure. The zone of the loop fastener attachment means, ATM1-A is shown on its top.

In the left side of this figure the loop fastener attachment means, ATM1-B is shown that attaches to the end of the strap, STR by the zone of hook fastener attachment means ATM2-RC on a detachable, re-attachable basis. The very end of the adaptor, ATM1-B has zone of hook fastener attachment means, ATM2-RB in its lower surface.

Importantly, the fact that the trapezoid piece is attached to the end of the strap by the hook fastener attachment means, ATM2-RC on a detachable, re-attachable basis, is important since it allows the position and the angulation of this piece compared to the end of the strap, STR to be adjusted. Also it is important that the end of the strap, STR attaches to the support, SUP by use of the zone of the hook fastener attachment means ATM2-RA, on a detachable, re-attachable basis. This allows the position and the angle of the attachment of the strap, STR to the support, SUP to be adjustable.

Figure 6:
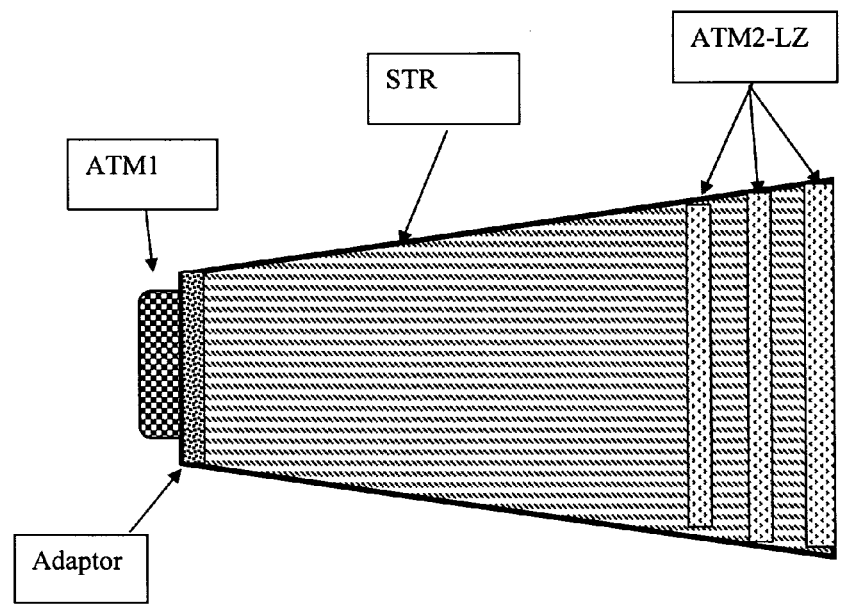
FIG. 6. Shows a strap means with smaller end piece that allows the hand of humans to grip the end and apply easily and zones of ATM2.

FIG. 6. Shows a strap means which has a rather trapezoid shape so that it can support a larger area of the body but reduces at its end so that the hand of humans can handle it easily. In this model also the outer surface of the strap, STR has multiple zones of hook fastener attachment means, ATM2-LZ which allows the incoming body of the strap, STR to attach to it on detachable, re-attachable attachment basis, after wrapping around the limb. The wide end of this strap, STR, shown in this figure at right side, will attach to the support, SUP (not shown in this figure) by one of the following means.

1. Being fixed on the support by a method such as being sewed.
2. By having a zone of hook fastener attachment means, ATM2 similar to the one in the right side of this strap but in its rear surface.
3. By any other means.

The narrow end of this strap, STR, shown in this figure at left side, has an end piece marked as the adaptor means, Adaptor, that allows it to attach to a zone of hook fastener attachment means, ATM2-V, (shown best at next figure) which also has a zone of loop fastener attachment means, ATM1 at its outer surface. The adaptor transforms the wide side of the strap to a smaller zone of hook fastener attachment means, ATM2-V which allows this end to attach to the support, SUP or a part similar to the loop fastener attachment means, ATM1-A on this strap on a detachable, re-attachable basis.

Figure 6A:
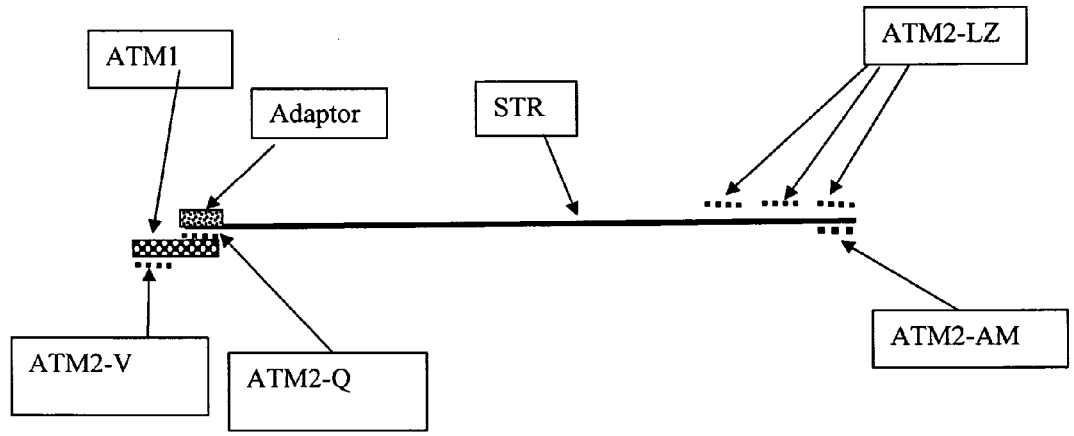
FIG. 6A. Shows the cross cut side view of the strap means, shown in previous FIG. 6.

FIG. 6A. Shows the cross cut view of the unit shown at FIG. 6. In this view the strap is shown at STR, the hook fastener attachment means ATM2-AM is in its lower surface, shown at right side of the figure. Three hook fastener attachment means, ATM2-LZ are located on its upper surface, shown at right side of the figure. The adaptor, Adaptor, is shown in the left side and attaches the end of the strap, STR to a piece made of loop fastener attachment means, ATM1 by use of hook fastener attachment means, ATM2-Q on a detachable, re-attachable basis. ATM2-Q, is shown in the left side of this figure. The loop fastener attachment means, ATM1 has a zone of hook fastener attachment means, ATM2-V in its rear/lower surface which allows this end to attach to the support, SUP or the ATM1. The adaptor piece is the end of the strap, STR that has an upper zone made from ATM1 and a lower zone made of hook fastener attachment means ATM2.

Figure 7:
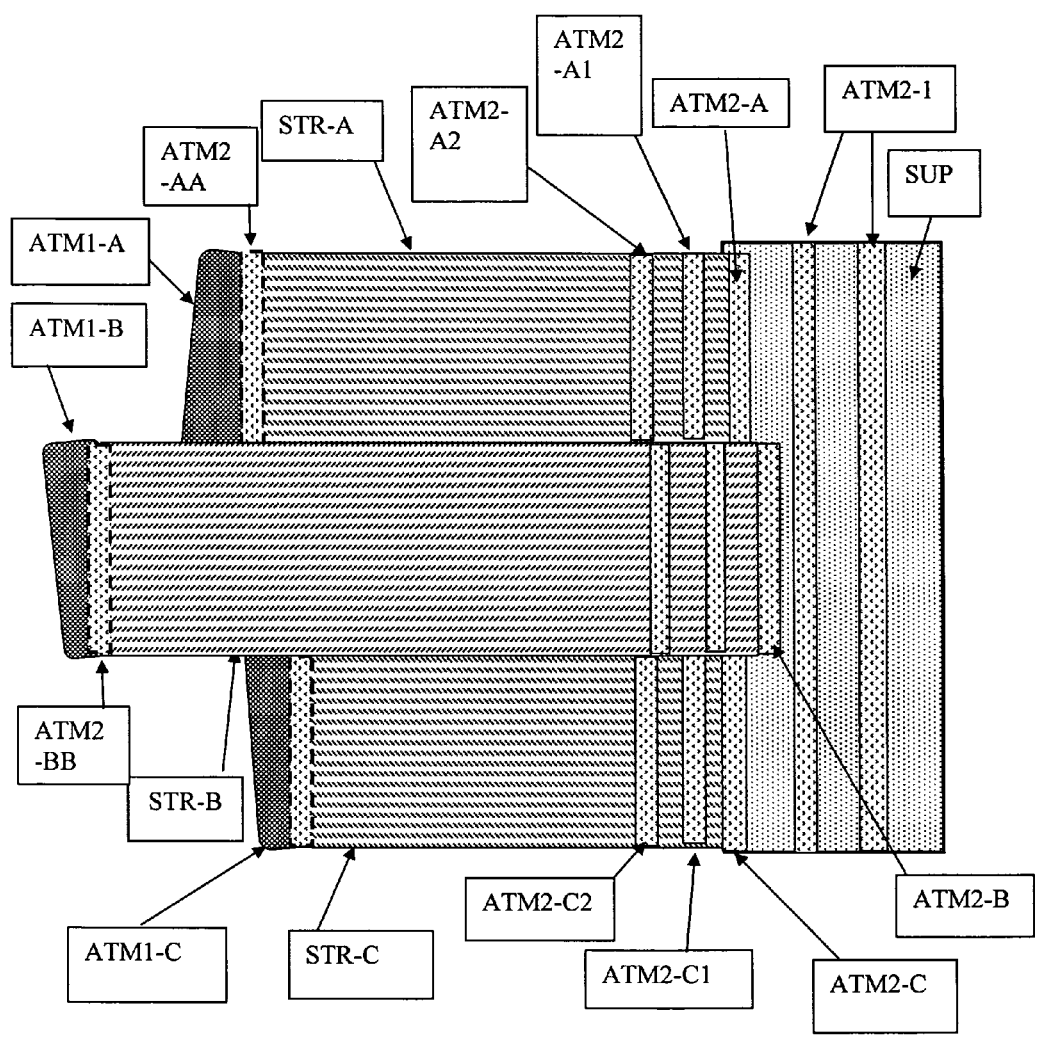
FIG. 7. Shows a support means with three wide strap means attached to it.

FIG. 7. Shows schematically a support means, SUP with three strap means, STR-A, STR-B and STR-C similar to the unit shown at previous figure except with a different shaped end pieces. This combination is for use in a limb such as arm or the leg. In this model a support made from a laminate or similar will be placed in front of the leg and a series of straps similar to the straps shown at FIG. 5 or 6 are attached to the support. The size and the shape of the end of the straps are designed to allow a comfortable placement on the leg, which mostly has a bulged area in the upper part and a thinner part in the lower end. In this model the outer surface of the straps has a series of zones of the hook fastener attachment means, ATM2-A, ATM2-A1 and ATM2-A2 for the strap, STR-A so that the end of the strap can attach to these zones after wrapping around the leg. The straps first will attach to the support and if they were long then the end pieces will attach to these hook fastener attachment means, attachment zones.

Two types of attachment will be functional.
1. The body of the straps, STR will attach to the hook fastener attachment means, ATM2 from the support and the outer surface of the straps.
2. The end piece of the strap means which has hook fastener attachment means, ATM2 will attach to the body of the support which is made of loop fastener attachment means, ATM1.

This mechanism will create a double attachment and a very secure attachment.

The end of the straps, such as STR-A may also attach to the outer surface of a double sided loop fastener attachment means, ATM1-A by use of a zone of hook fastener attachment means, ATM2-AA so that this allows the direction and position of the line of attachment of the strap means, STR-A to the ATM1-A to be adjusted. Then the lower surface of the end piece ATM1-A will also attach to the zones of hook fastener attachment means ATM2 located at the outer surface of the support and initial outer surface of the straps, such as the strap STR-A or STR-B.

The use of such units have the following advantages.
1. They are easy to use.
2. They are easily adjustable, since the straps can be adjusted individually.
3. The method provides overlaping of straps so that it prevents from one segment of the leg to be without compression between its distal and proximal piece which will create stagnation of blood and clot formation.
4. Further adjustablility is possible by re-positioning of different pieces and segments of these units.

Figure 8:
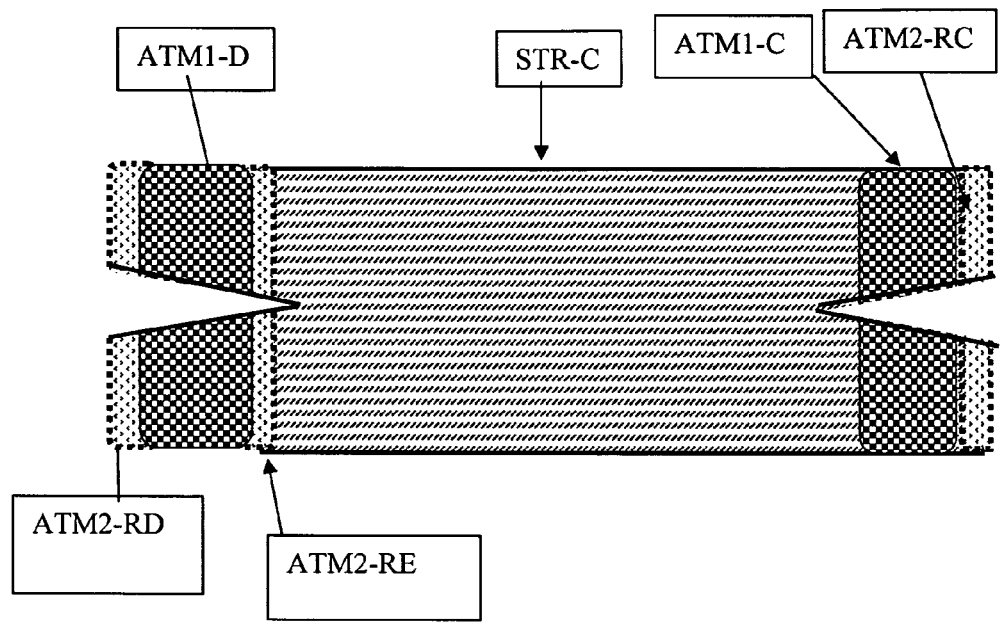
FIG. 8. Shows a wide strap means with cut at the end and two tongues.

FIG. 8. Shows a wide strap means similar to one shown at FIG. 5 except in this model the end pieces of the strap has a cut creating two tongues. So that it allows the position of the attachment of each tongue to be decided.

The use of this model with a support has the following advantageous.
1. Allows the strap to be used in a bulged area.
2. Allows the end of the strap to be handled easily, while one end is attached the other one can be released.
3. Allows a wide strap to be handled with ease.
4. Allows one end to be pulled more than other when beneficial.
5. Allows one end to be attached to the support in an angulated fashion.
6. It allows one end to attach to the outer surface of the other end at ATM1-C or ATM1-D when this attachment is needed in certain conditions.

In this model the strap, STR-C has a wide rectangular shape that has a wedge shaped cut at the end of the strap and each end has a tongue consisting a hook fastener attachment means ATM2-RC in its rear surface (shown at right side of the figure), that allows it to attach to the support, SUP on a detachable, re-attachable basis. Next to the end in left side there is rather wide zone of loop fastener attachment means, ATM1-C that allows the attachment means, ATM2-RD at the end piece of the strap, STR-C to attach to it after wrapping over the support, SUP (not shown in this figure) and if the strap was long and if such attachment was needed to control the extra length of the strap, STR-C. The same thing is true about the other ends as well. Thus this method transforms the wide side of the strap to a smaller zone of hook fastener attachment means, ATM2-RD. The ATM2-RD allows this end to attach to the support, SUP or the loop fastener attachment means, ATM1-C of this strap on a detachable, re-attachable basis. This method with the smaller end of this piece allows the hand of the users to hold it more securely and comfortably. This method allows two or more straps to be used in order to cover the leg and to have the straps to overlap each other for preventing from gaps between the straps.

Figure 8A:
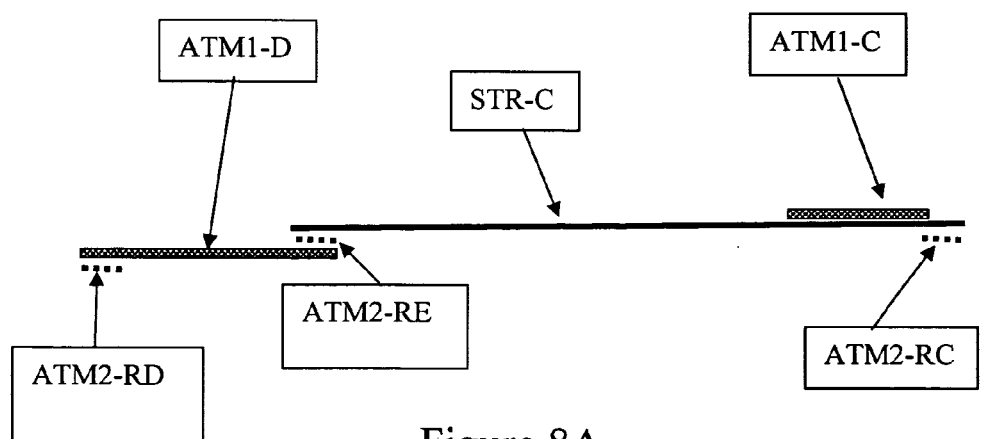
FIG. 8A. Shows the cross cut view of the unit shown at FIG. 8.

FIG. 8A. Shows the cross cut view of the unit shown at FIG. 8. In this view the strap is shown at STR-C, the hook fastener attachment means ATM2-RC is in its lower surface, shown at right side of the figure. The zone of loop fastener attachment means, ATM1-C is shown on its top.

In the left side of this figure the loop fastener attachment means, ATM1-D is shown that attaches to the end of the strap, STR-C by the zone of hook fastener attachment means ATM2-RE on a detachable, re-attachable means. The very end of the adaptor, ATM1-D has zone of hook fastener attachment means, ATM2-RD in its lower surface.

Importantly, the fact that the adaptor is attached to the end of the strap by the hook fastener attachment means, ATM2-RC on a detachable, re-attachable basis, is important since it allows the position of the end piece compared to the end of the strap, STR-C to be adjusted. This attachment can be permanent as well. Also it is important that the end of the strap, STR-C attaches to the support, SUP (not shown in this figure) by use of the zone of the hook fastener attachment means ATM2-RC, on a detachable, re-attachable basis. Since this allows the position and the angle of the attachment of the strap, STR-C to the support, SUP to be adjustable.

Figure 9:
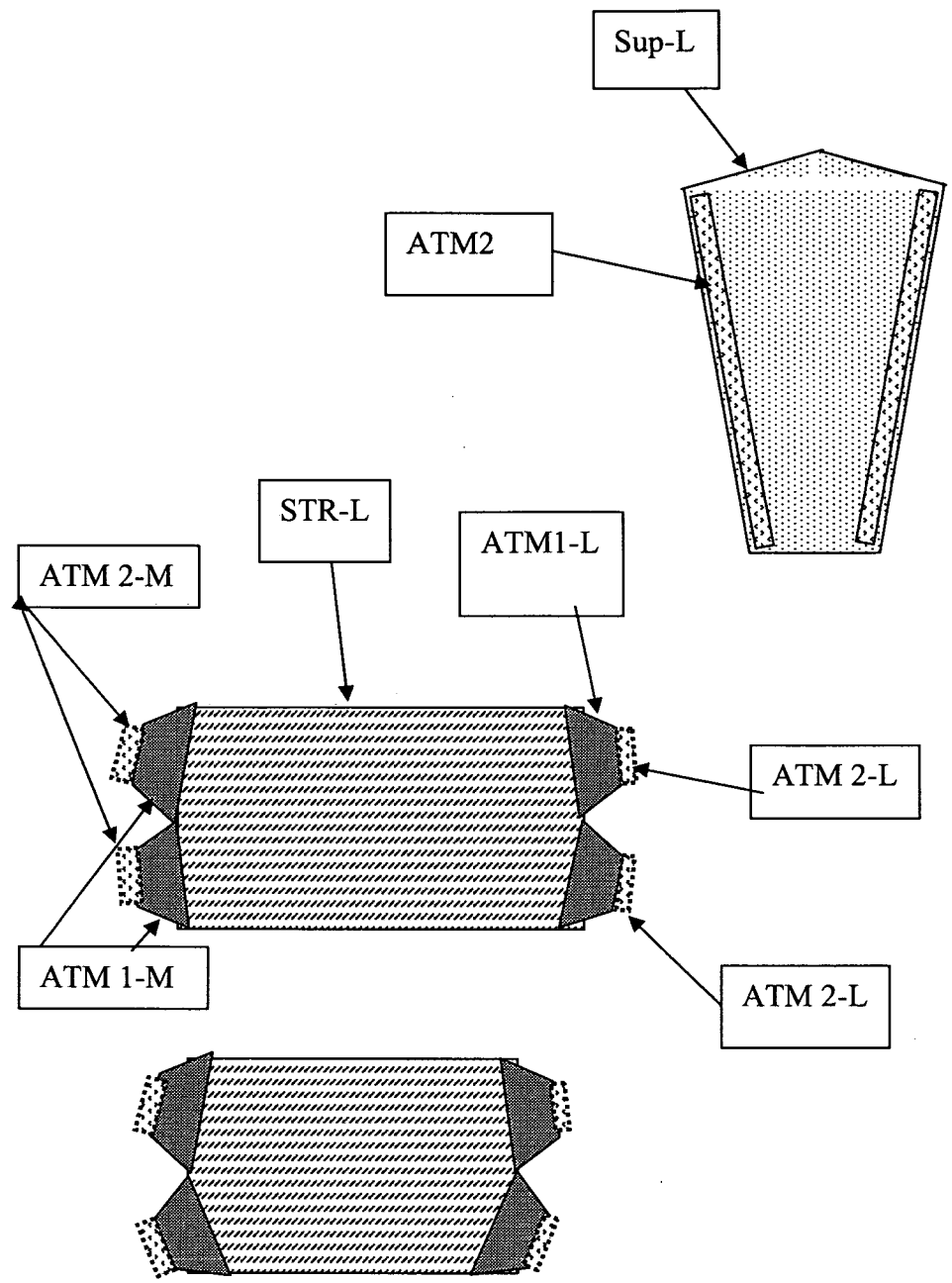
FIG. 9. Shows a special support for leg with two wide strap means with cut at the end and two tongues.

FIG. 9. Shows a support, SUP-L designed for the support of the leg. The support, SUP-L, has a rather trapezoid shape with a longer width on the top and narrower width in the bottom so that it allows the upper part to be placed on the upper leg and the narrower part in the lower front leg which has a smaller circumscance. The straps will be attached to it to cover the sides and rear proportionally. This unit has the advantage that matches the size of the limb. The support has an outer layer made from a loop fastener attachment means, ATM1 with zones of hook fastener attachment means, ATM2 on it. This allows the strap made from lycra with an attachment means at the end to be attached to it in two ways.
A. The body of the lycra will attach to the zones of the hook fastener attachment means, ATM2.
B. The end of the strap which has the hook fastener attachment means, ATM2 will attach to the outer surface of the body of the support on a detachable, re-attachable basis.

This unit uses one or more straps in order to cover the leg without leaving an uncovered space.

An example of the strap is shown at FIGS. 8 & 8A. With some modification.

This figure shows a wide strap means with a cut and two tongues at its ends, so that it allows the position of the attachment to be decided.

This model has the following advantageous.
1. Allows the strap to be used in a bulged area.
2. Allows the end of the strap to be handled easily. While one end is attached the other one can be released.
3. Allows a wide strap to be handled with ease.
4. Allows one end to be pulled more than other when beneficial.
5. Allows one end to be attached to the support in an angulated fashion.
6. It allows one end to attach to the outer surface of the other end at ATM1-L, ATM1-M or other similar areas when this attachment is needed in certain conditions.

In this model the strap, STR-L has a wide rectangular shape with some modification that has a wedge shaped cut at the end of the strap in each side. Each end has a tongue consisting a hook fastener attachment means, ATM2-L and ATM2-M in its rear surface, that allows it to attach to the support, SUP-L on a detachable, re-attachable basis. Next to the ends pieces there are a rather wide zone of loop fastener attachment means, ATM1-L and ATM1-M which allow the attachment means, ATM2-L or ATM2-M or similar at the end piece of the strap, STR-L to attach to them after wrapping over the support, SUP and if the strap was long, and if such attachment was needed to control the extra length of the strap, STR-L. The same thing is true about the other ends as well. Thus this method transforms the wide side of the strap to a smaller zone of hook fastener attachment means, ATM2-L and ATM2-M. The ATM2-M allows this end to attach to the support, SUP-L or the loop fastener attachment means, ATM1-L, ATM1-M or similar of this strap on a detachable, re-attachable basis. This method allows two or more straps to be used in order to cover the leg and to have the straps to overlap each other for preventing from gaps between the straps. Importantly, in some models the support, SUP-L may also have a zone of adhesive in its back in order to allow the support to be adhered to skin and prevent it from moving done. Alternatively the YD pieces may be used as well.

Importantly, in some models the zones of the ATM2 will have a rather rigid body in order to prevent the support from shrinking.

Importantly, the support, SUP-L may also have a zones of attachment means to allow other units such as, pads, balloons, etc. to be adhered to it on a detachable, re-attachable basis.

The lower strap is similar to the upper strap except has a smaller size.

Importantly, the unit may also have a rigid piece in front to protect the leg from trauma.

Figure 10:
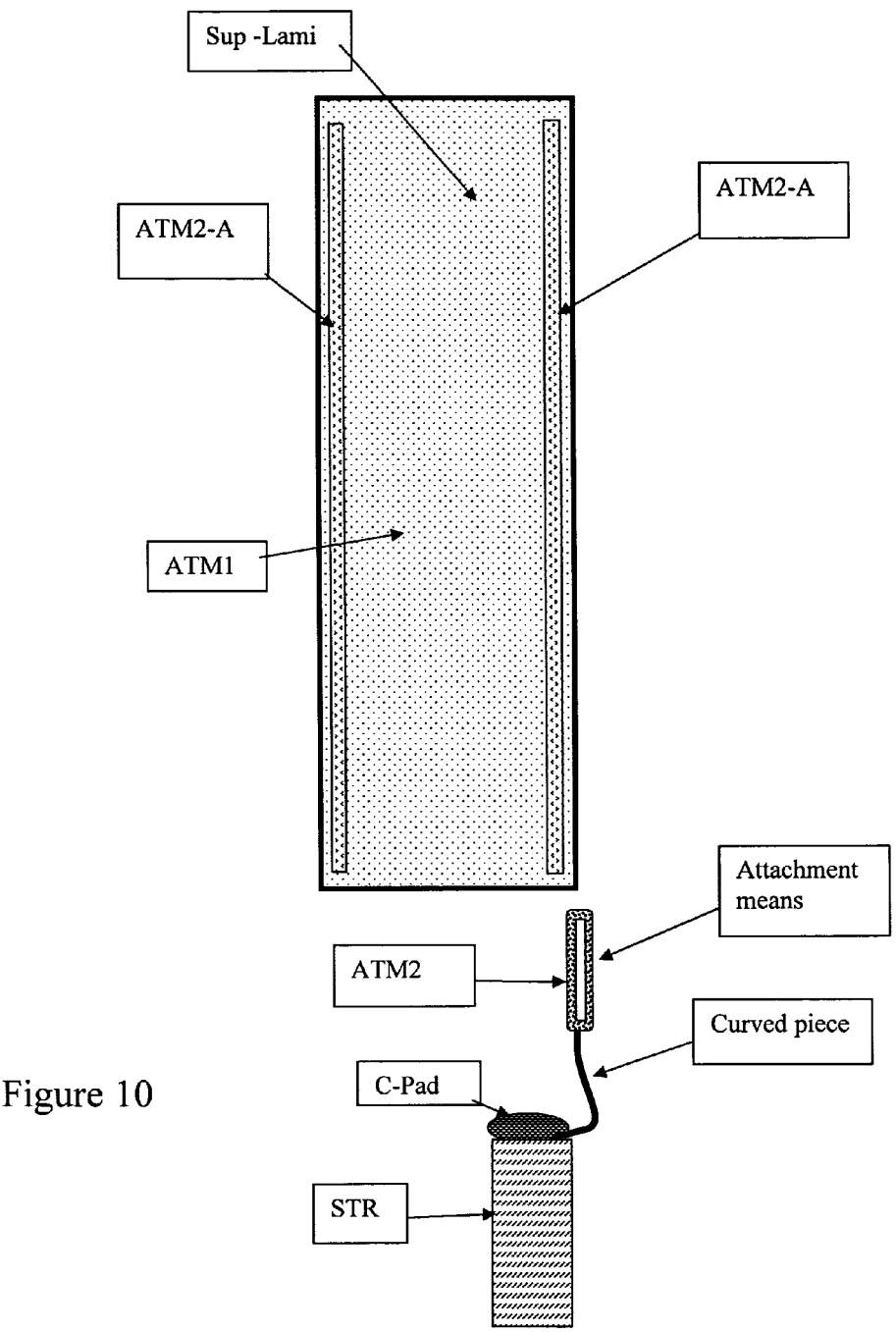
FIG. 10. Shows a support means, SUP, made from a non-stretchable layer with an extension piece for the leg.
Figure 10:
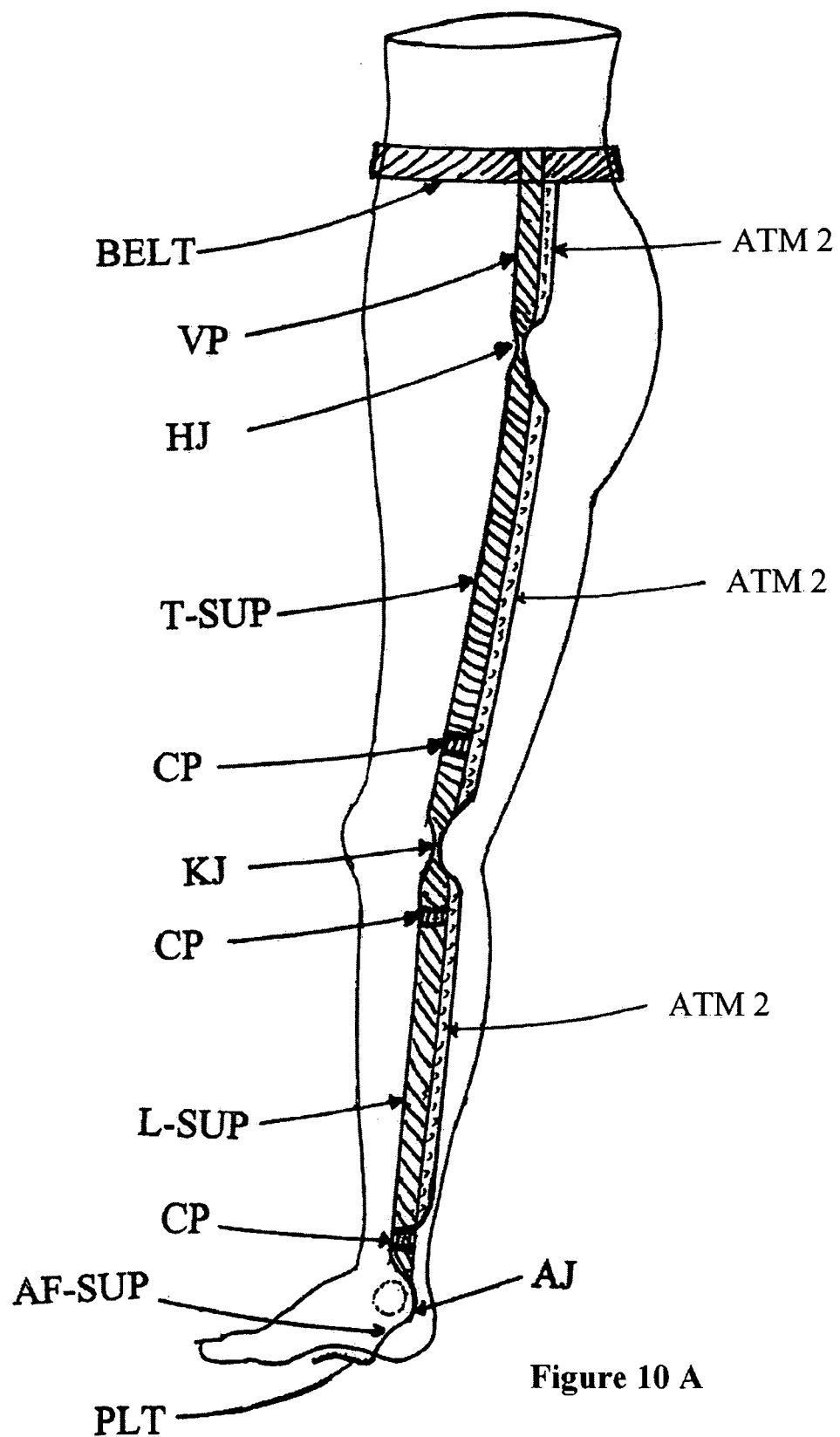

FIG. 10. Shows a support means, SUP, made from a laminate mentioned to the support means explained earlier. The support may have zones of hook fastener attachment means, ATM2, as shown, which allows straps made from Lycra, TM, to be attached to it on detachable/re-attachable basis.

Importantly, the hook fastener attachment means, ATM2 can be made in different versions.
1. To be made from a double sided hook fastener attachment means, ATM2, that allows it to be removed and re-attached on detachable, re-attachable attachment means. This allows the position of these pieces to be changed easily.
2. Such ATM2 pieces may be made to be cut easily so that their length can be modified easily.
3. They can be made to be relatively rigid in order to prevent from deformation and shrinking of these units and the attached support unit length wise.
4. They may have extensions in order to prevent from the movement of the support to unwanted areas such as dropping of the support to the foot area when they are placed on the leg. The extension will go to the sole area and keep this unit stable. A sample is shown in this figure and the piece has a base shown at C-Pad that stands under the arch of the foot. The C-Pad has a strap means, STR that will wrap around the foot and keep this piece in place, also the strap, STR will compress the feet to prevent from engorgement of the veins and lymphatic system of the feet. A shaped extension piece, here referred as the Curved Piece connects the foot piece to the body of the support, SUP on a detachable, re-attachable basis, by use of attachment means, Attachment means. The attachment means has a body of its own and here they are made from hook fastener attachment means, ATM2 and will attach to the body of SUP on detachable, re-attachable attachment basis. The shape and size of the support and its structure may vary to feet different part of the body.

Importantly, by covering the feet, ankle and the leg this unit will prevent from the expansion of the venous system and lymphatic in this area and related complications.

FIG. 10A. Shows schematically a support mechanism, designed to support the strap means in the thigh, leg and ankle-feet area. This unit consist of.
1. A belt, BELT made from a non-stretchable material that stands in the belt area and allows a vertical piece, VP to be attached to it on a detachable/re-attachable basis. The belt, BELT prevents the vertical piece, VP from moving down.
2. A vertical piece, VP made from a non-stretchable material that moves down from the belt, BELT and attaches to joint means at hip joint area, HJ and attaches to the support means designed to stand on the thigh area, T-SUP. The VP prevents the thigh support, T-SUP from moving down.

Figure 10B:
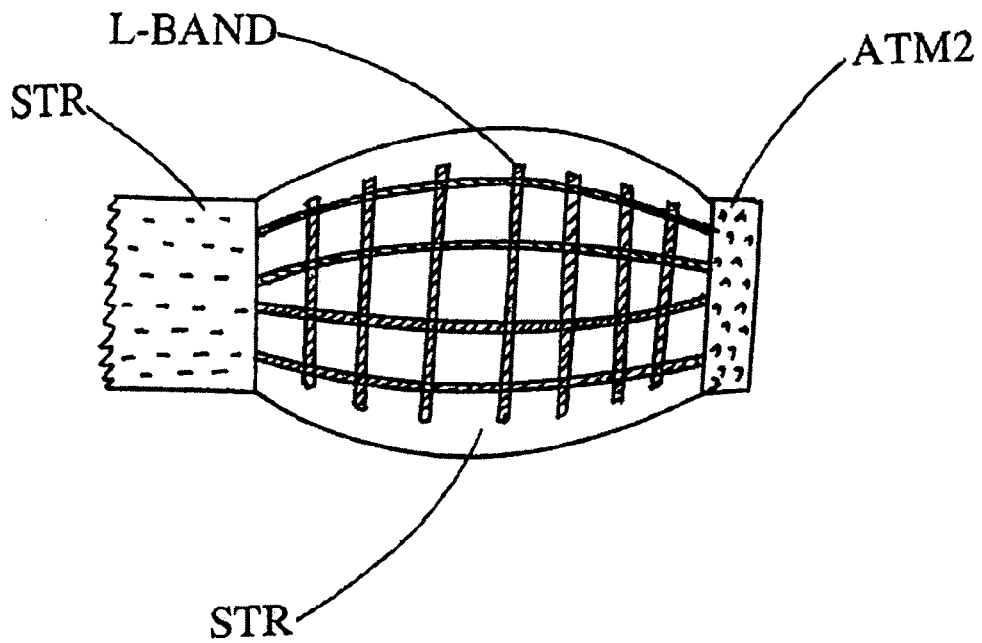
FIG. 10B. Shows a shaped strap means fortified with an skeleton made from an elastic material.
Figure 10C:
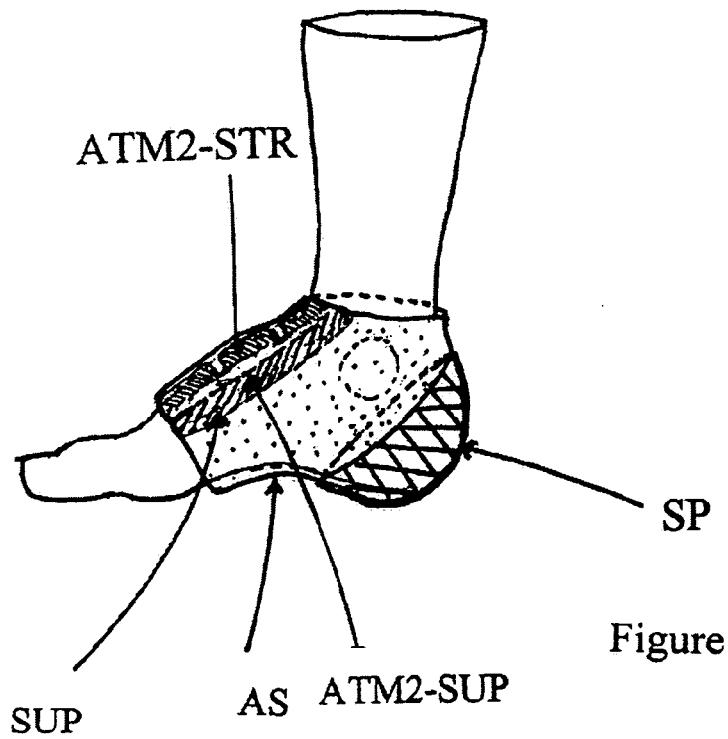
FIG. 10C. Shows a shaped strap means with a support means for the ankle foot area.

Thus the hip joint means, HJ stands between the vertical piece, VP and the thigh support, T-SUP.
3. A thigh support, T-SUP made from a relatively, non-stretchable material which functions as the support piece in the thigh area and will move down from the piece for the hip joint, HJ and attach to a joint means in the knee joint area, KJ. This support, T-SUP allows multiple strap means to be attached to it on a detachable/re-attachable basis. The T-SUP prevents the leg support, L-SUP from moving down. Importantly, the size and shape of this support may vary. For example the outer surface of the body may be covered with loop fastener attachment means, ATM1 in order to allow the end of a strap means with ATM2 to attach to it on a drab. Also the zone of hook fastener attachment means, ATM2 will allow the body of the strap means to attach to it on a drab. The body of this unit may be relatively rigid in order to prevent from shrinking of this piece. Thus this unit will provide stability to the whole system and will keep the strap means in the area as desired. The unit may have more zones of hook fastener attachment means, ATM2 for allowing the strap to attach to it for example in the knee area. Also this support may also combined with other supports in order to complement each other for more supportive function. The extra supports may be placed in other side of the limb or any other area as needed for further support. The unit may have a shaped support to fit the knee cap area in order to keep the strap in the knee area more securely. The shaped part may be made from screen made from rubber, latex or similar means to have a shape body yet to be able to adapt the shape of the area and stretch as well. Importantly, the shaped piece may be part of the strap as well as shown in FIGS. 10B and 10C.

4. A leg support, L-SUP which is made from a relatively, non-stretchable material which functions as the support piece in the leg area and moves down from the joint means for the knee joint, KJ and attaches to the ankle-feet piece in ankle joint area, AJ. This support, L-SUP allows multiple strap means to be attached to it on a detachable/re-attachable basis. This piece will keep the straps in stable condition and prevents them from moving down.
5. An ankle-feet support, AF-SUP made from a relatively, non-stretchable shaped material as explained earlier in this application and this unit will prevent the leg support, L-SUP from moving down. The shape of ankle-feet support, AF-SUP matches the shape of the anatomy of the area and it stands in the ankle-foot area and moves down to the sole of the foot and is kept in place by use of series of straps that wraps around the foot. These strap means keeps this piece in place also will compress the soft tissue of the ankle-feet area.
6. Importantly, a series of functional joint means such as the HJ, KJ and AJ are utilized in this unit in order to allow the upper and lower pieces to rotate in these joints. These joint means can be a spring means, a relatively, thin polymer or any other means that can be utilized in these areas that allows the unit to be held stable yet to function as a joint.
7. This figure also shows a foot hose, FH which is stretchable and will fit and compress the feet. This piece has a zone of ATM1 that allows the end of the strap means for the leg or the leg and thigh etc. To be attached to it and then to wrap around the ankle and move up to the leg and thigh. A shaped unit for the foot-ankle area is shown at FIG. 10C.
8. A series of connection means such as CP are designed to allow the two pieces of the supports to be attached to each other on a detachable/re-attachable basis.

Importantly, this support system will be modified to fit the special needs for example in order to use this support means with the unit shown at FIG. 4 the body of this support means may have an outer cover made from loop fastener attachment means, ATM1 to allow hook fastener attachment means, ATM2 to attach to it. Also it has zones of hook fastener attachment means, ATM2 that allows the strap means to attach to it after wrapping around the limb and be kept in place by the support securely. The unit can be modified for use with multiple straps as well.

This method allows one support or more to be utilized if needed. FIG. 10B. Shows the front view of a special stretchable support unit which is made from modification of the body of a strap made from the LYCRA (TM). In the model shown here the body of the strap is modified by use of relatively narrow bands or an elastic screen made from elastic materials such as latex as shown at L-BAND. Importantly, modifying the strap by this method or reshaping it by other means such sewing or other means allows a relatively stretchable, shaped support to be made. Such a support is useful in areas with a particular shape and function, such as knees, ankles, elbows, toes, etc. This shaped, stretchable support allows better handling and placement of such units and provides the following advantages:
   a. In this model the support has a relatively, stretchable body which allows it to be pulled to keep it in place with a comfortable tension. This mild, comfortable tension is an important property for use in these areas and will keep the properties of the joint together and allows motion as well. The shape of this unit will adjust itself with the changing body of the underlying tissue such as the joint.
   b. The support unit stretches and conforms to accept the shape of the area. Also, such a body allows this body of the support to change with change of the wound areas such as over joints such as the knees, ankles, hips, elbows with extension and closure.
   c. The inner part of the support is a soft, non-irritant fabric and does not cause skin reaction.
   d. This model allows an easy placement of this unit on a prominent area of the body such as scalp or a joint as shown in the model for the ankle and allows an easy and rather quick dressing of the wound. Also they will be more stable in the area.
   e. Importantly, the side where the strap is attached stretches in both direction and allows this unit to fit a shaped area, such as the scalp or over a joint. Importantly, a complementing transverse strap allows this unit to be further stable on the scalp. This will make a cross-shaped unit.

In this figure the attachment means of the support is shown at ATM2 and the strap at STR. A D-Ring may be unutilized so that it will allow the length of the strap to be adjusted.

FIG. 10C. Shows schematically a support means designed for wound dressing of the ankle area. This unit is a modified version of a unit which is shown in this application for the wound dressing of the ankle and consists of.
1. A support means, SUP designed to stand in front of the very lower leg and/or the upper part of the ankle and upper part of the foot as shown. The support means, SUP is made from a non-stretchable layer similar to the supports which are explained in this application previously. In this prototype model the support, SUP is made from a laminate, with a surface made from ATM1 that allows the hook fastener attachment means, ATM2, to be attached to it on detachable/re-attachable basis. A soft lining for being placed on the skin or cover of a wound and a layer of a foam sandwiched in between as it is explained more in this application.
   The support means, SUP, has a rather rectangular or trapezoid shape, has a long, narrow zone of hook fastener attachment means, ATM2-SUP on its border that allows a strap made from Lycra, TM or a zone of loop fastener attachment means to be attached to it on detachable, re-attachable basis.
   Also Importantly, the end of the strap, has a zones of hook fastener attachment means, ATM2-STR that attaches to the outer surface of support, SUP, on a detachable/re-attachable basis. Please note that in this model the support, SUP is made from a laminate, with a surface made from ATM1 that allows the hook fastener attachment means, ATM2, to be attached to it on detachable/re-attachable basis. The end of the strap means, ATM2-STR is cut to function as tongues, here the unit has 3 such tongues, that allows each one to be pulled and attached to the out surface of the support, SUP, independently, which makes the adjustment easy.
   Importantly, this method will make a double attachment means that allows a very unique and stable attachment of the strap, STR, to the support, SUP, on a detachable/re-attachable basis and makes the attachment of the strap to support far more easy.
2. A rather wide strap means, AS, made from an stretchable fabric, LYCRA TM, which is shaped and sized to conform around the ankle and attach to the support, SUP, by use of a zone of hook fastener attachment means, ATM2-SUP on a detachable/re-attachable basis. The body of the strap, AS, functions as the loop fastener attachment means and attaches to the zone of the ATM2-SUP on a detachable/re-attachable basis.
3. A special piece, SP, made from an elastic skeleton made from a material such as a latex is attached to the body of the strap means, AS in order to conform the strap means, AS, to shape it as desired and make it to accept the heel and fit the heel easily. AS was explained in previous FIG. 10B. By doing so, it will secure the position of the strap means, AS in the heel and will allow an easy placement of this unit on the heel. So that the strap means, AS can be easily pulled to be attached to the hook fastener attachment means, ATM2-SUP of the support, SUP. Thus by doing so the whole placement of this unit will be easier and the unit will stay on the area more securely, since the shaped, special, piece, SP, will not allow the unit to move to sides while it is being kept in place by the stretchable strap means, AS.

Importantly, this method plays a crucial rule in keeping such units in prominent areas such as heels, knees, shoulder, scalp, elbows, and any similar places. This idea was previously explained to be utilized in other areas such as the knee and can be used in any other site that can be utilized.

Importantly, the shaped piece may be embedded to the body of the strap, or it may be attached to it by various means. It may have a body made from a screen of latex or similar material or it can be a shaped, stretchable layer. Importantly, it may be made in any form, shape or material that will serve this purpose.

Importantly, the special piece, SP, can be attached to the body of the strap means, AS on a permanent or detachable/re-attachable basis.

Method of Use.
1. At the time of use initially the user will place the special piece, SP, from this unit on the heel of the person.
2. Then will pull the support, SUP, gently to place on the upper surface of the ankle, foot area. Please note that the support, SUP is attached to the strap means, AS.
3. The user will then pull end pieces, ATM2-STR of the strap, AS and attach the body of the strap, AS to the attachment zone ATM-SUP of the support means, SUP on a detachable/re-attachable basis and will continue to pull the rest of the end pieces ATM2-STR to the support in a similar way.
4. Then the user will pull the end pieces, ATM2-STR of the strap, AS and attach them to the outer surface of the support means, SUP on a detachable/re-attachable basis and will continue to pull the rest of the end pieces ATM2-STR to the outer surface of the support in a similar fashion.

Figure 11:
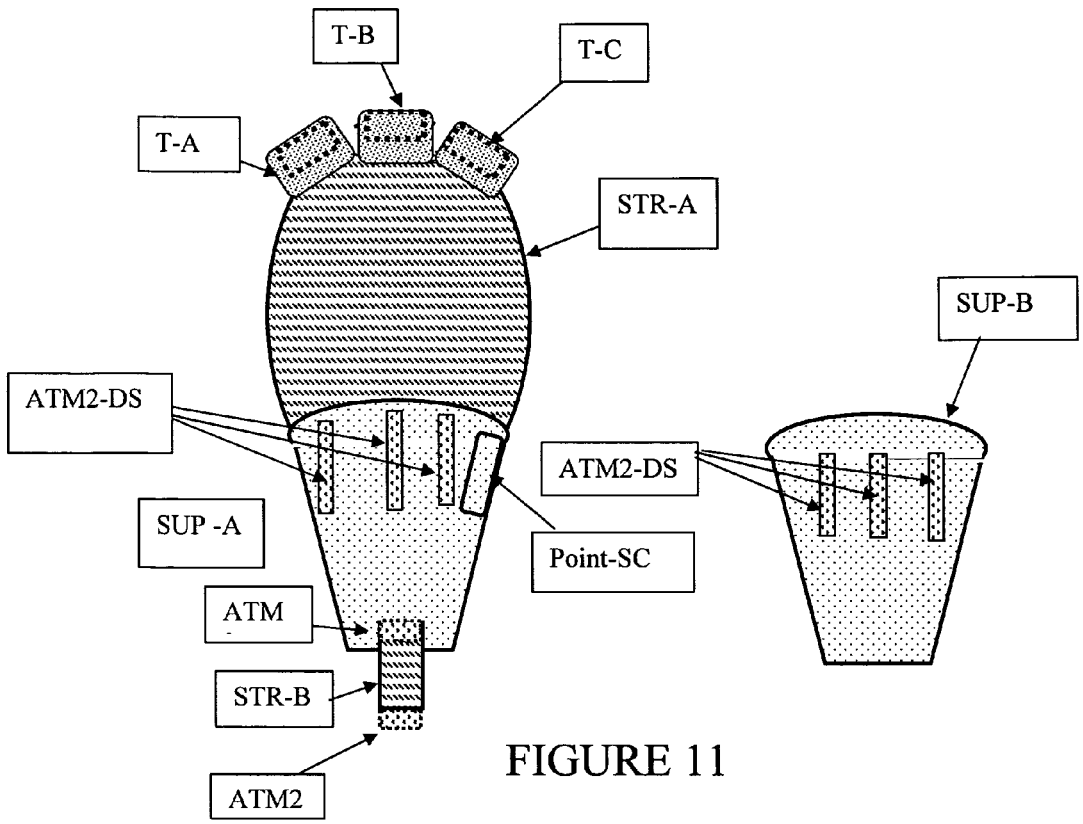
FIG. 11. Shows a support means designed for use in the head.

FIG. 11. Shows the use of more than one support and strap combination for use in more complicated areas. In this model two shaped supports, SUP-A and SUP-B made from laminates are used to stand in the sides of a limb or in this case the faces. One of the supports, SUP-A has a wide strap, STR-A attached to it on rather permanent basis, although this can be on a detachable, re-attachable attachment basis, as well. The other end of this stretchable strap, STR-A has a three tongues, T-A, T-B and T-C which have an outer surface covered with loop fastener attachment means, ATM1, (The ATM1 is optional in this part) and an inner surface which has a zone of hook fastener attachment means, ATM2, the border of this zone if shown by a dotted line, that allows this unit to attach to the outer surface of the support, SUP-B on a detachable, re-attachable attachment basis. A smaller strap, STR-B allows the lower ends of the supports, SUP-A and SUP-B to be hold securely in place and allows the tension of this system to be adjusted. Importantly, due to the shape of these pieces this unit will sit on the head and keep the dressing on the vertex and head comfortably and steadily, particularly when the matching support, SUP-C and strap means for the head, STR-H which will wrap around the head and attach to these supports on detachable, re-attachable attachment basis, and will make a very secure unit.

Figure 11A:
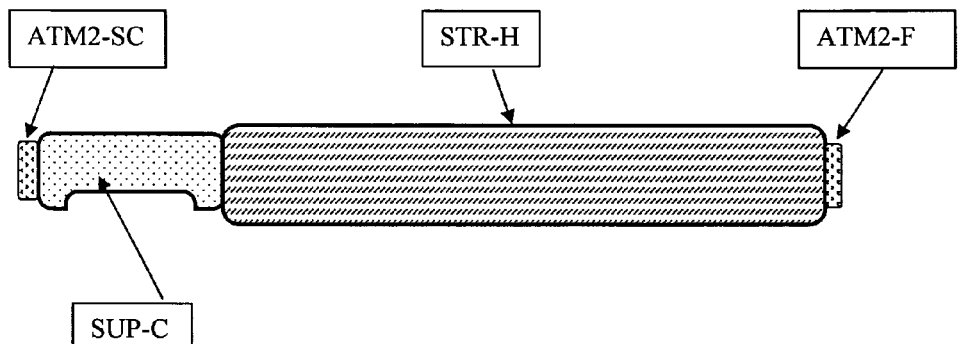
FIG. 11A. Shows a complimentary strap means for use with the unit shown in previous FIG. 11.

The support, SUP-C strap means, STR-H shown in FIG. 11A.

FIG. 11A shows a unit for placement in front of the head of the user.

Which is also a complimentary support strap means for the unit shown in FIG. 11.

This unit consist of a strap, STR-H that wraps around the head horizontally and comes and attaches to the support C, SUP-C and by doing so it prevents the whole unit from moving up and down toward the vertex of the head or toward the chin. Thus the whole unit will have secure attachment and will hold them stable on a detachable, re-attachable attachment basis. The support, SUP-C is made from a laminate and has a design for standing on the frontal part of the head of the person without blocking his/her eyes. One end of this support has a zone of hook fastener attachment means, ATM2-SC that allows this unit to attach to the front border of the outer surface of the support, SUP-A at Point SC shown in previous FIG. 11 on a detachable, re-attachable attachment basis. The other end of the support, SUP-C is attached to a rather wide stretchable strap made from Lycra (TM) that has a size for wrapping round the head horizontally, in order to attach to the zones of ATM2-DS from the outer surface of the support, SUP-B on detachable, re-attachable basis and go over occipital area and to come to attach to the ATM2-DS on the outer side of support, SUP-A and also the end piece of the strap, STR-H, shown at ATM2-F will attach to the outer surface of the support, SUP-C on a detachable, re-attachable basis. Importantly, during the wrapping process the inner surface of the stretchable, head strap STR-H will attach to the zones of the double sided, hook fastener attachment means, ATM2-DS on the outer surfaces of the supports, SUP-A and SUP-B on a detachable, re-attachable attachment basis. This kind of attachment will keep the supports in position and prevent it from moving back and forth. Importantly, the zones of the hook fastener attachment mean on the outer surfaces of the supports, SUP-A and SUP-B are made from double sided, hook fastener attachment means, DS- ATM2 so that they are attached to the outer surfaces of the supports, SUP-A and SUP-B on a detachable, re-attachable basis, basis. Thus these pieces can be removed, cut, re-positioned etc. in order to size them properly and place them as they can function best. Importantly, these pieces have a lower surface made from a double sided, hook fastener attachment means, DS-ATM2 which has more grip so that they are attached to the outer surfaces of the supports, SUP-A and SUP-B on a detachable, re-attachable attachment means, basis but will need more force to be separated. But the outer surface of these double sided, hook fastener attachment means, here reffered as, DS-ATM2 and shown at FIGS. 4D, 4E and 4F has a zone of hook fastener attachment means, DS-ATM2 with a lesser grip so that they allow the strap means, STR-H to be attached to them on a detachable, re-attachable attachment basis, basis but to be released easily before the DS-ATM2 will disengage from the outer surfaces of the supports, SUP-A and SUP-B. What happens is that since the lower surface of the DS-ATM2 has more surface covered with is piece shown at those figures at ATM2-B and also has more grip as it is chosen to, the strap will detach from the ATM2-A of these units without causing the rigid piece to detach from the support.

Importantly, the strap, STR-H is wide in order to cover the occipital area of the head and the adjacent areas, it has a smaller end pieces in order to allow it to be grabbed and hold easily.

Importantly, this method can be modified for use in other parts of the body which can be useful for example in cases which the patient had amputation of the foot or the hand this unit can be used more effectively, particularly with use of pieces shown at FIGS. 12-13. FIG. 12. Shows use of more than one support and strap combination in complicated areas. In this model a support, SUP-M which has a zone of adhesive, ADH in its rear surface (shown at FIG. 12A) is designed for being adhered to skin. The purpose is for the adhesive to prevent from the support, SUP-M from falling or displacement.

Method of Use.

One support, SUP-M1 will be placed on one side of the limb and a similar support may be also placed on the other side of the limb. This allows a rectangular or a shaped strap with attachment means, ATM2 at its ends to attach to one of these supports and go over the amputated area, make a U turn and then to attach to the body of the other support, SUP-M2 on a detachable, re-attachable, basis.

FIG. 12A. Shows the side view of the support, SUP-M shown at FIG. 12. In this view the body of the support is shown with a loop fastener attachment means, ATM1 on its surface and zones of double sided, hook fastener attachment means, DS-ATM2. The lower/rear surface of this support has a layer of adhesive, ADH.

FIG. 13. Shows combination of two supports, SUP-E and SUP-F in a joint. This design is t the unit to be used on a joint area when the amputated area or the wound area is close to the joint such as knee and does not leave space for the support to be placed in the area. In this model the support, SUP-E will be adhered to the skin on the area above a joint such as knee and another support, SUP-F will be placed on the skin in an area below the knee so that these two supports will be attached to each other by use of a band, Band. The band, Band is attached to the surface of the first support by use of hook fastener attachment means, ATM2.

The upper support will be attached above the joint and the lower support will be below the joint (on the upper leg area) and this allows the joint to move and the supports to be functional while the patient is standing, since the band will prevent from the second support from falling. This will allow a rectangular or a shaped strap with attachment means, ATM2 at its ends to be used with two supports, such as support F. One of such supports, SUP-F1 not shown in the figure will be placed in one side of the amputated leg and the other support, SUP-F2 will be placed on the other side of the amputated leg. Then the strap will be attached to one of these supports such as SUP F1 and go over the amputated area, make a U turn and then to attach to the body of the other support similar to the support-F here reffered as SUP-F2 on a detachable, re-attachable, basis.

The area may use one of such combination or two of them depending to the condition and the location of the wound.

FIG. 14. Shows few pad means designed for use with the supports.

The pad means may have different sizes, shapes, thickness and stiffness and other important characteristics. They may be made from inflated or inflatable balloons. They may be made for being attached to the support and the straps in order to be placed under the support and over the wound for various reasons. Thus these pads may be made.

1. A padding with various body, gauze pad, absorbent etc.
2. A balloon with various shapes such as the flat, more round etc.
3. An inflatable balloon that allows the pressure inside the balloon to increase.
4. A shaped balloon, or pad. To apply certain compression in wound.
5. A medicated pad. To deliver medicine to the person.
6. An absorbent pad to allow the drainage of the wound to be absorbed.
7. A sticky pad to adhere to the wound.
8. A pad with nonporous membrane such as vinyl.
9. A pad which has an adhesive tape.
10. Heated pad or cold compresses.
11. They can be made from rigid, clear acrylic in order to allow compression of the wound and vision. It may have hole or opening to allow a needle to pass thorough. These units may be particularly suitable for conditions such as the sclerotherapy of the spider veins.

The pad means have a attachment means such as the ATM-X that allows the pad means to be attached to the support or strap means. The attachment means can be of various forms such as; adhesive, snaps, fastener means, bands etc. So that it can allow the pad means to be re-positioned or exchanged. Also importantly, the pads may be attached to the wound area by adhesives or bands so that then the support can be placed on them and compressed by use of the straps.

The model in the right side of the figure shows a pad, Pad with adhesive tape, Adhesive Tape attached to it. This model allows the cover of the adhesive to be removed along the dotted line so that the pad can be adhered to the skin by use of the adhesive tape. This allows the pad to stay on the wound so that the support can be placed on the top of the pad and the straps to be wrapped on the site. This can be useful in cases such as the injection for the superficial varicose veins in order to provide compression on the vein site.

Importantly, the pad may have different thickness or consistency for applying different level of pressure to the wound. Example of this is shown in right side, this unit has a smaller, thicker central pad piece shown with a dotted circle and a thinner, or softer larger piece shown in large circle. Such a unit allows the center of the wound to be compressed more. Different sized or shaped units may be made for other uses. The characteristics of these pad may vary in many ways to satisfy different needs.

Also Importantly, the pads may be made to be medicated pads, in order to deliver medication to the wound or even to an intact skin for systemic absorption. Also they may provide heat or cold to the wound by use of heated pads, heated units or cold compresses.

FIG. 15. Shows two support means that are attached to each other by use of a detachable, re-attachable method. In this figure the second support, SUP-2 is attached to the first support, SUP-1 by use of fastener attachment means. This method shows that two or more support can be used with each other for various reasons; change in shape, size etc. In this model the rear surface of the SUP-2 has loop fastener attachment means, that allows it to attach to the hook fastener attachment means, ATM2 of the first support, SUP-1.

Figure 17:
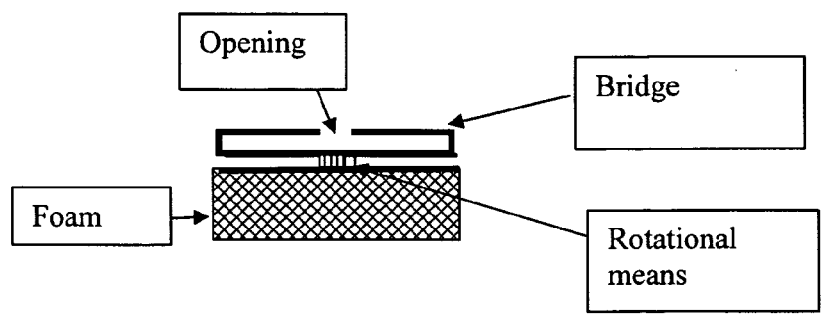
FIGS. 17 and 17A. Show a pad means with a bridge in its rear.

FIG. 16. Shows two support means that are attached to each other on a detachable, re-attachable basis, by use of a strap means. In this figure the support means are shown at SUP-3 and SUP-4 and the strap means at STR. The strap means is attached to the supports by use of fastener attachment means. This method shows that two or more supports to be attached to each other for various reasons and on adjustable basis. FIG. 17. Shows a method which allows a pad means or a foam, Foam to be placed under a strap when the strap is already on the limb and also to be moved or removed and rotated. In this method a bridge, Bridge, with opening, Opening is attached to the back of the pad means or foam by a rotating means, Rotational means. The bridge allows this piece to be placed under the strap and the strap to be feed under the bridge by use of the opening. The rotational means allows the foam to be rotated in a desired direction.

Figure 17A:
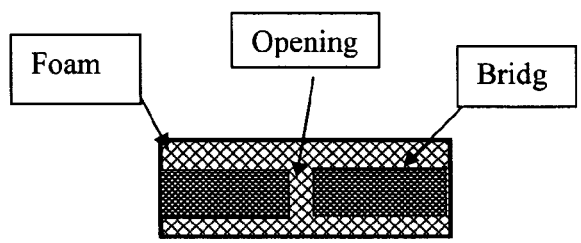
Figures 18, 18A:
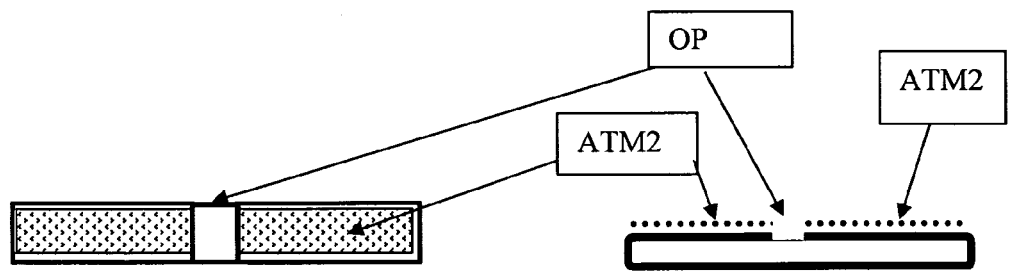
FIGS. 18 & 18A. Show a bridge with attachment means on its rear surface.

FIG. 17A. Shows the top view of the unit shown at previous FIG. 17. FIG. 18. Shows a means which allows a bridge shaped means with a zone of hook fastener attachment means, ATM2 on it to be placed under a strap means when the strap is already on the limb and allow the coming strap with a ATM1 type property to be attached to it on a detachable, re-attachable basis. In this method the body of the bridge, Bridge, is shown with an opening, OP on it. The bridge allows this piece to be placed under the strap and the incoming strap to be attached to the hook fastener attachment means, ATM2 of the outer surface of the bridge.

FIG. 18A. Shows the side view of the unit shown at previous FIG. 18.

Figure 19:
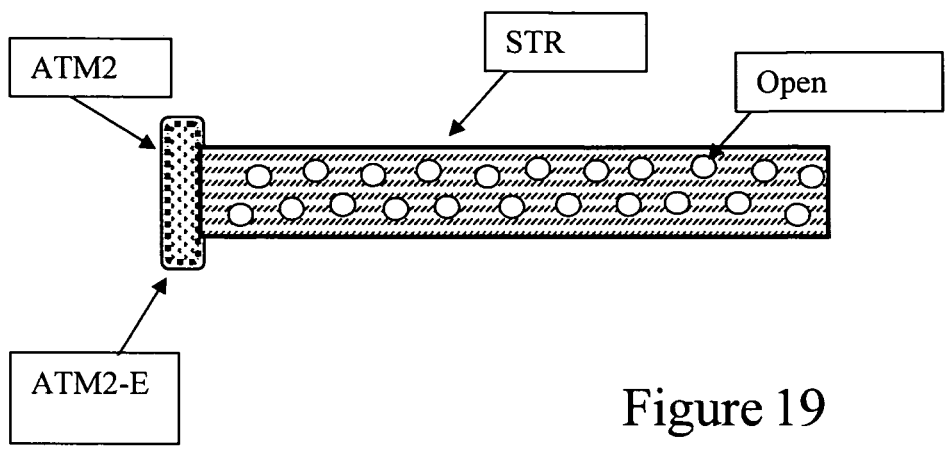
FIG. 19. Shows a strap means with holes in body and extended attachment means in one end.

FIG. 19. Shows two properties, 1. The strap means has a series of openings, Open that allows the air to move for ventilation.

2. it shows a method of control of the end piece of the strap means, STR, by use of a long zone of hook fastener attachment means, ATM2 in its rear/lower surface, shown with a dotted border. However, the ATM2 extends in each side like a ear, ATM2-E So that this allows the extended pieces to be folded over the body of the underlying strap, when the strap has wrapped on the limb and reaches over the first wrap of the strap, STR itself. The folding this ear piece will make
A. The end piece to attach to the shiny surface of the strap, STR. which is on the limb.
B. After the attachment the ear pieces will be squeezed between two layers of the strap and the skin so that the attachment and the squeezing force will keep the end piece stable and prevent it from moving.

Figure 20:
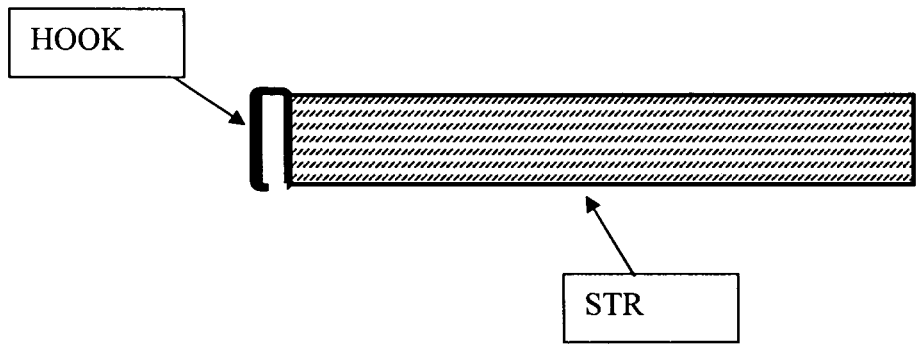
FIG. 20. Show a hook means at the end of a strap means.

FIG. 20. Shows another method of controlling the end piece of the strap means, STR. In this method the free end of the strap, STR has a hook means, Hook that will be placed under the first wrapped part of the strap, STR and the limb under. The outer surface of the hook means will have a indentations similar to the hook fastener attachment means, ATM2. Thus it will attach to the shiny surface of the overlying strap on a detachable, re-attachable basis. Thus the hook will
A. Have attachment to the body of the shiny piece of the strap, STR. and resist the move. B. This piece will be squeezed between the two layers of the straps and the limb under, so that with attachment and the squeezing force it will be kept stable and will not move.

Figure 21:
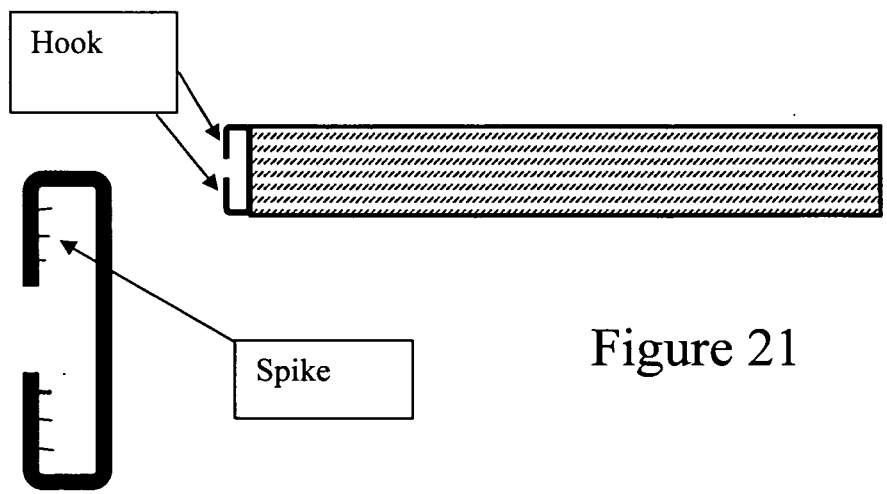
FIG. 21. Shows a strap with other form of hook means at the end.

FIG. 21. Shows another method of controlling the end piece of the strap means, STR. In this method the free end of the strap, STR also has a hook, Hook which has a bent at each ends. These bent parts have fine spikes, Spikes at its body placed so that it will be placed under the first wrapped part of the strap, STR and the body. Importantly, the spikes are made in a part of the hook, Hook that will not touch the body. Thus this hook will
A. Have a contact with the body of the shiny piece of the strap, STR. and resist the move. Since the spikes, Spikes of these end pieces will engage the body of the strap on detachable, re-attachable means.
B. This piece will be squeezed between two the strap and the body, so that with attachment and this squeezing force it will be kept stable and wound not move.

Very, importantly, please note that the straps means referred in this application are made from a stretchable fabric commonly called Lycra and is now available in the US. This stretchable fabric is a woven fabric that has the lycra in it with other material such as nylon ect. In his research course the applicant noted that this material is capable of stretching and detachably/re-attachably directly attaching to the support through detachable/re-attachable contact of a shiny surface of the Lycra (TM) fabric with the hook fastener attachment means. Thus he made supports with the Velcro (TM) attachment means on its outer surface. Thus the attachment means on the support comprises a suitable hook-type material, such as Velcro. The Lycra (TM) fabric has a dull (non-shiny) surface opposite the shiny surface. Because of the inventor's discovery of the properties of lycra, a strap made from it is both stretchable and directly attachable and detachable to the support so that attachment can be made with different degree of stretching and different distances along the length of the strap, and without any special attachment device attached to the Lycra.

FIGS. 22 and 23. Show schematically, new methods and means of application of the straps means to a limb in a far easier fashion. So that both the application and the removal of such straps will be easy and manageable. FIG. 22. Shows schematically, a hand held unit which the applicant has designed in order to allow a wrap such as the strap or these units to be applied to a limb and removed from the limb with significant ease. This unit may have different versions. The version the shown in this FIG. 22 consist of a rectangular shaped, rigid layer, Rigid Layer which has a zone of loop fastener attachment means, ATM1 on it. Pieces of pads, Pad are placed in the sides of this unit to provide more body and grip to this unit. The zone of loop fastener attachment means, ATM1 may be on one or more of these pads or the body of the pads may be even made with an outer surface made of loop fastener attachment means, ATM1. This zone allows the end of the strap means STR-F from the FIG. 4 or 4AB which has a zone of ATM2 to be attached to it on detachable, re-attachable basis, and to be wrapped around it.

Method of Use.
1. At a time which the strap is not in use and needs to be kept in a condition for use the first free end of the strap, STR-F (shown at FIG. 4 or 4AB) which has a zone of ATM2 will be attached to the body of this unit and the strap will be wrapped around this piece so that finally it will be in a compact stable condition.
2. At the time of delivery the second end of the strap which will be free at this point will be attached to the body of the support, SUP and the strap will be unwraped from this unit and wrapped around the limb till finally its end piece will be attached to the outer surface of the strap means, itself as designed. The applicant may provide a movie showing these functions in future if the USPTO examiner will allow.

FIG. 23. Shows schematically, a second unit which is even better, in this model the unit has a hand held unit which has a cylindrical, or cuboid shape body, Cylinder in the model shown at left side and Cuboid piece Shown in the right side of this figure. These parts has a handle, Handle for being hold in hand. The outer surface of the cylinderical or the cuboid body of these units has a zone of loop fastener attachment means, ATM1 which allows the end piece of the strap means STR-F from the FIGS. 4, 4AB or similar which has a zone of ATM2 to be attached to it on a detachable, re-attachable basis.

Method of Use.
1. At the time of storage which the strap needs to be kept in stable condition the zone of ATM2 from first free end of the strap, STR-F will be attached to the zone of ATM1 of the body of these units and the strap will be wrapped around the body of these units so that finally it will be totally wrapped around the body of these units and will be hold in a compact, controlled fashion.
2. At the time of delivery the second or the free end of strap will be attached to the body of the support, SUP and the strap will be unwraped from the boy of these units and wrapped around the limb while being both pulled and wrapped, till finally it's end piece will be attached to the outer surface of the strap means, it self as designed. The handle may be made to move and hide inside the body of this unit to save space for storing or packaging etc.

Importantly, this makes the process of the application and the removal of these units very significantly easily and manageable and the applicant may apply for a patent in this regard.

Figure 24:
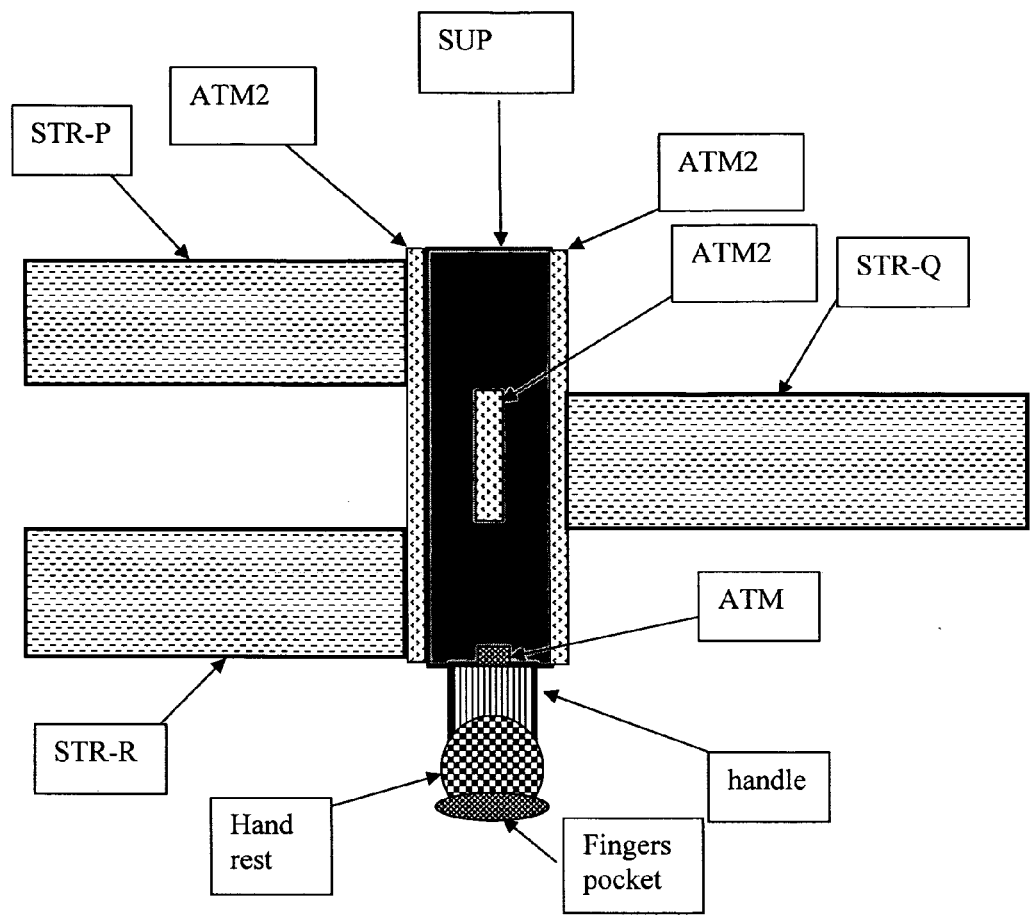
FIG. 24. Shows support, strap means with a hand rest.

FIG. 24. Shows schematically a support means, SUP with a series of strap means, STR-P, STR-Q and STR-R which are attached to the support. The support is made from a laminate or similar and is designed to stand on the front of the arm. The support has a hand piece, Hand rest that attaches to the support by a handle. The hand rest has a space, Fingers pocket that allows the fingers to be sited inside for easy control and holding the support. The straps will wrap around the support and hold the unit in place securely as well as compressing if needed. Other pieces such as a rigid piece may be attached to the support at ATM2 on the support on detachable, re-attachable, basis. Further straps can be attached to the hand rest for holding the hand. This unit will be useful for immobilizing the hands and wrist in conditions such as fractured hands. This unit can be folded to be in a compact condition for being carried. The straps will wrap around the limb and will be attached to the support by use of similar to the other units explained in the application. The use of such units have the following adva 1. They are easy to use.
2. They are easily adjustable, since the straps can be adjusted individually.
3. The method provides a compact protective unit for use in emergencies.
4. Further adjustablility is possible by movement of the hand pieces in different direction and re-positioning of different pieces and segments of these units.

FIG. 25. Shows a method of attachment of the strap-support means to the body of the uniform of a personal so that it allows the unit to be grabbed and used in a very short time in a man made or natural disaster that the time is of extreme importance. In this model the body of the envelope of these units will be attached to the uniform of the staff on a detachable, re-attachable basis, that allows the user to grab, detach and use the wound supports, Wound Sup.

FIG. 26. Shows a method of combining these supports with supports that cover the following areas. This support has a tubular, hose type body that can be pulled over a joint such as the knee or over the thigh and leg area etc. Thus the use will provide a mean of controlling the strap mean. This model can be modified to be used in following anatomical parts for example in the.

A. The knee area,
1. By having this support-strap means to go over the knee or
2. By having a house type stretchable unit that will attach to these units by different attachment means
3. By having a strap means with a shaped piece to stand on the knee cap area to be stable and to allow the strap to wrap on it to be held in place securely.

B. The thigh area.
1. By having this support-strap means to move up and wrap around the thigh. The support to have an attachment to the belt system to prevent it from falling.
2. By having a house type stretchable unit with pants commonly used for the sports so that the lower part of tit will attach to these units by different attachment means.

C. The foot-ankle area.
1. By having this support-strap means to go over the feet and ankle and to attach to this unit by having the extension of the support and wrapping the straps.
2. By having a tight socks that will attach to these units by attachment means 3. By having a strap means to go around the foot and wrap and then to be attached to the leg unit on detachable, re-attachable attachment basis.

FIG. 27. Shows a unit that has a line of attachment that allows the cover of this unit to be hold and to be opened in the process of removal from the attached area of this unit. In this method the attachment of the part of the pocket to the holding unit is strong and allows the pulling to tear the pocket of the unit. This method will hold a clean or sterilized strap means inside and to be pulled to be applied to the limb when needed.

Figure 28:
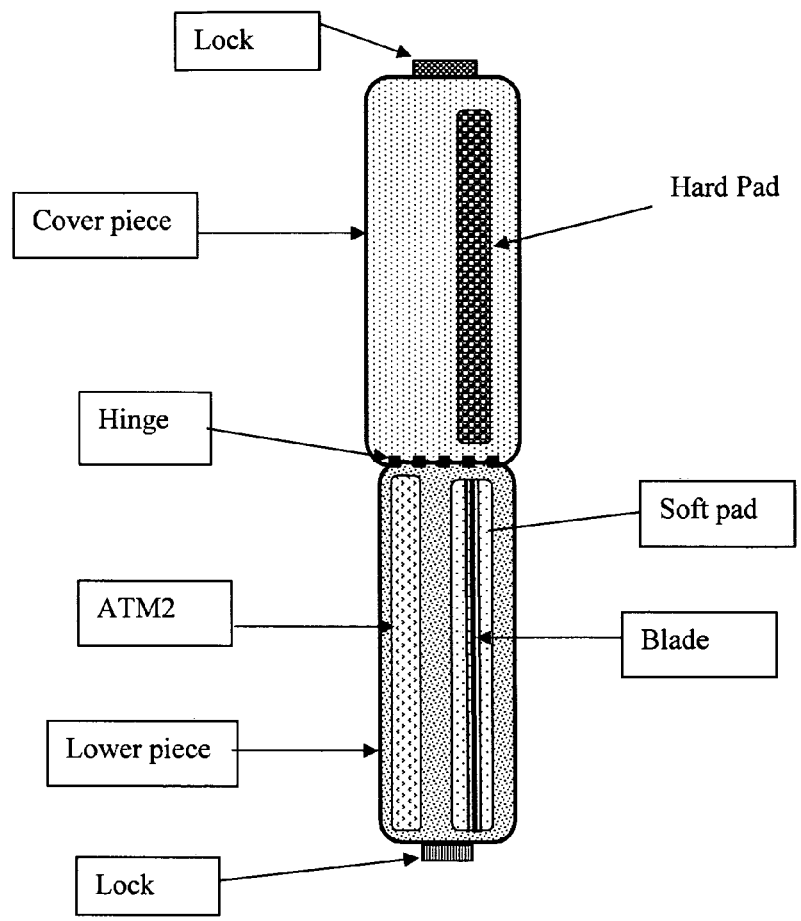
FIGS. 28 & 28A. Show a unit for cutting the end of a strap.

FIG. 28. Shows a unit designed for allowing an end piece of a strap means, to be placed inside this unit and to have the extra piece to be cut. This unit consist of two pieces the upper cover piece, Cover piece and a lower piece, Lower piece which are hinged together at Hinge. The lower surface of the lower piece shown at FIG. 28A has a zone of loop fastener attachment means ATM1 shown at FIG. 28A, so that it allows this piece to be attached to the hook fastener attachment zone, ATM2 of the support. When in place on the support this unit will allow the strap, STR to be pulled and attached to the hook fastener attachment means, ATM2 of the lower piece, Lower piece on a detachable, re-attachable basis.

The lower piece has a hidden blade, Blade in between a soft pad, Soft pad that when compressed by the hard pad, Hard pad from the cover it will cut the strap located between these two pieces.

FIG. 29. Shows another unit designed for allowing the end piece of a long strap to be cut to a size. Please also note the rear view of this unit is shown at FIG. 29A and the cross cut view at FIG. 29B. This unit allows the cut end to be modified so that the end piece will be.

1. in proper size so that the length of the strap will be ideal and not short or long and to fit the angulation of the area.
2. To allow a nice end piece to be left after cutting
3. To allow the end piece to be attached to the support or the body of strap on a detachable, re-attachable attachment basis.

For this purpose the applicant has designed the piece shown at these figures. This piece consist of a relatively rigid material the relative thickness is shown at FIG. 29B at R-Rigid. Which its rear surface shown at FIG. 29A is covered with hook fastener attachment means, ATM2-R. The front or the top surface of this piece has two smaller zones of hook fastener attachment means, ATM2-U and the ATM2-V. The zone of the hook fastener attachment means, ATM2-U covers more than the half of the front surface of this piece and the ATM2-V has a narrower zone of hook fastener attachment means. A free space without hook fastener attachment means, shown at NO-ATM2 separates these two zones from each other. This unit has the following use.

Method of Use.
1. The front surface of this piece will be attached to the support, SUP on detachable, re-attachable attachment basis.
2. The strap will be pulled to attach to the ATM2-R at rear surface of this piece. When the position of the strap is adjusted to be optimal. Then the user
3. Will separate this piece and wraps the strap STR and attaches the end strap, STR to the ATM2-V.
4. The user cutter the extra end of the strap, STR by placing the seizures or any other means of cutting, blade, heat, sharp wire etc. in the free space, NO-ATM2 and cuts the extra piece of the stra This leaves a nicely cut end piece that can be attach to the support by use of ATM2-U.

Importantly, instead of the attachment means, ATM2, and adhesive layer will function to do the job although the ATM2 will be easier since eliminates the removal of the cover of adhesive and also allows multiple adjustments before cutting the end piece. Adhesives also are difficult to be used with gloves.

Figure 30:
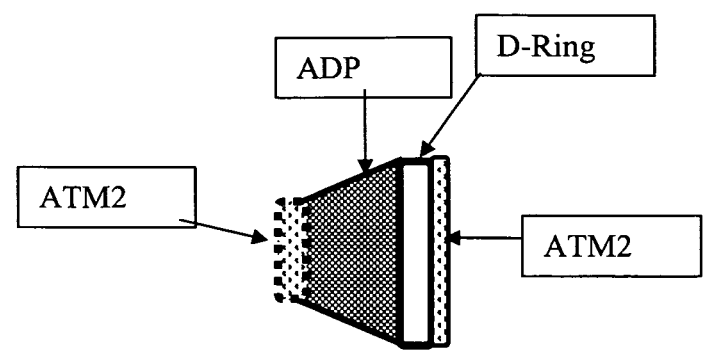
FIG. 30. Shows an end piece for the strap which makes it smaller.

FIG. 30. Shows a D-ring, D-Ring that allows the wide end of a strap means to be wrapped around it, make a U turn in the wider side of this unit and attach to the rear surface of its own. This unit has a piece, reffered as the adaptor, ADP that transforms a wide strap means to a smaller end means shown at ATM2. The zone, ATM2 allows the end of this unit to attach to the outer surface of the support on a detachable, re-attachable basis. This unit can be utilized in a unit shown at FIG. 4A.

Figure 31:
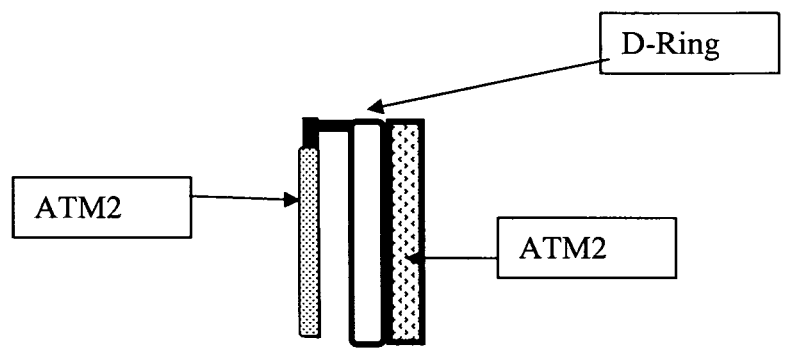
FIG. 31. Shows an end piece for strap with a hook means at the end.

FIG. 31. Shows a D-ring, D-Ring similar to the unit shown at FIG. 30 that has a hook with ATM2 on it, this allows the hook to be placed under the strap as is mentioned in previous figure. This unit also allows the strap, STR to make a U turn in this unit and attach to the rear surface of its own.

Figure 32:
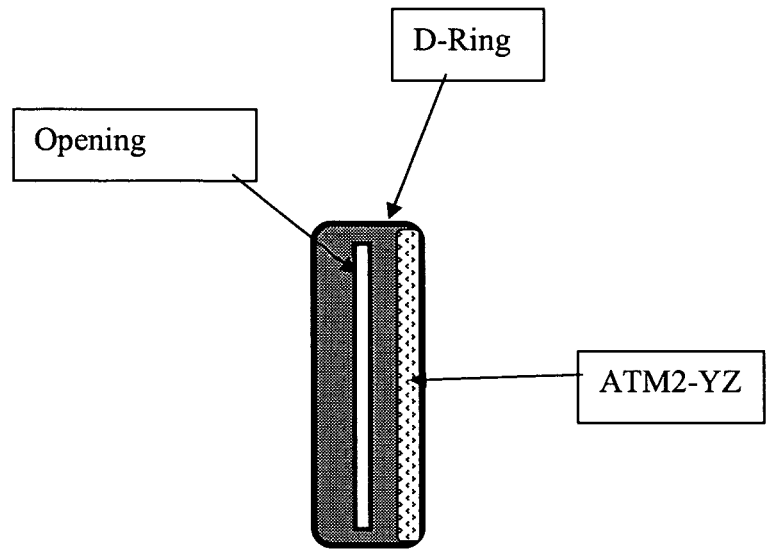
FIGS. 32 & 32A. Show a D-Ring for controlling the length a long strap.

FIG. 32. Shows a special D-ring, D-Ring that has a rather two wider surfaces in each side. It consist also a zone of hook fastener attachment means, ATM2-YZ on one surface of it in one side and ATM2-ZZ on the other surface. This allows the strap, STR to make a U turn in this unit and attach to the rear surface of its own. Also allows the zone ATM2-ZZ to attach to the outer surface of the support, SUP after wrapping around limb and this will keep the end of the strap means sturdy and neatly under control.

Figure 32A:
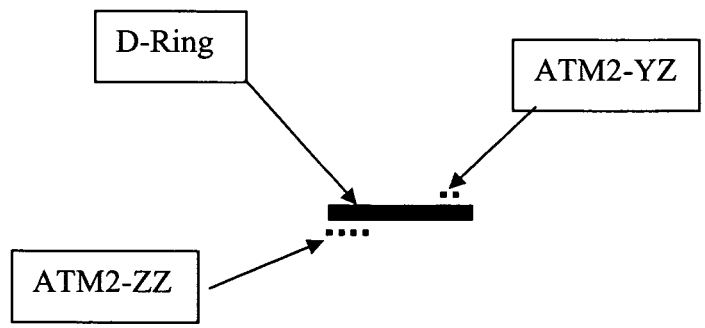

FIG. 32A. Shows the side view of the unit shown in FIG. 32. In this figure the D-ring, D-Ring is shown with zones of hook fastener attachment means, ATM2-YZ on one surface of it in one side and ATM2-ZZ on the other surface. Detailed explanation of this invention.

This invention shows a support, strap system that is a very versatile and allows a limb or a wound site to be dressed and wrapped by a quick and easy method. Please note that since many details are mentioned in the figures and not repeated in this part for using the space economically, those are part of the application as well.

This unit consists of:
1. A support means, SUP, made from a non-stretchable layer that has at least one zone of attachment means on its surface for allowing a strap means to be attached to it on a detachable, re-attachable basis. In this model this support means is made from a laminate, or any other material that has an outer surface made from loop fastener attachment means, ATM1 that allows the hook fastener attachment means, ATM2, to be attached to it on detachable/re-attachable basis, an optional, inner surface, made from a soft lining for being placed on the wound site or skin, and an optional layer of foam sandwiched in between. The support has zones of hook fastener attachment means, ATM2 that allows the body of special straps, STR to be attached to them directly.

In the prototype model, the attachment means of the support is made from zones of hook fastener attachment means, ATM2, as shown.

Commonly, the support, SUP, has a rectangular shape, although the shapes may vary. For example a trapezoid shape support is shown for the leg area.

The hook type fastener attachment means, ATM2 on the support allows a strap means made from Lycra, TM, to be attached to it directly, on a detachable/re-attachable basis. Importantly, the support may be made from a stretchable layer. Importantly, the unit may use more than one support as shown in FIGS. 4, 4B, 11, 11A, 12, 13, 15 and 16 for various reasons, such as use in difficult areas such as head, or in sides of joints such as hips, knees also for special use such as dressing an amputated area. The support may have adhesive in the back as shown in FIGS. 12 and 12A for reasons, such as preventing from the support to move or for keeping the support in place and re-using the strap means. The support may have two pieces attached to each other by use of a band or a strap as shown in FIGS. 13 & 16 to allow one support to be stable and the other one to move relative to the first one. The supports may attach to each other as shown in FIG. 15 for reasons, such as adjusting size, shape etc.

2. The unit may use at least one strap means, STR, made from an stretchable fabric that functions as an stretchable, loop fastener attachment means such as LYCRA,TM or similar. So that this strap has a special property that conforms to the shape of the area, and also has the very important property of being not only stretchable, but also it directly, attaches to the zone of the hook fastener attachment means, ATM2, from the support on a detachable/re-attachable basis. This is an extremely important and useful property and makes this unit unique.

Importantly, the strap means may have only one surface or both of its surfaces to have such property and to be able to be attached to the zone of the hook fastener attachment means, ATM2, on a detachable/re-attachable basis.

At present the available Lycra (TM) has only one side, which is shiny and is capable of engaging with the hook fastener attachment means, ATM2, the engagement of the other side, which is dull is much weaker and unpredictable. It is reasonable to believe that with use of the teaching from this applicant to further alter the manufacturing of this fabric in order to make this method more functional by.

1. Increase or decrease the capability of engagement of this kind of fabric to the hook fastener attachment means, ATM2.
2. To make special hook fastener attachment means, ATM2 that is more capable to engage with this fabric.
3. To alter this fabric in many ways, to make it thick, thin, with openings in it, etc.
4. To alter this fabric in order to have its dull side (both sides) to have zone of attachment means similar to the shiny side for engagement of the hook fastener attachment means, ATM2 or any other attachment means.
5. To alter this fabric to have both sides to be shiny for engagement of the hook fastener attachment means, ATM2 or any other attachment means.
6. AT present by sewing or attaching two layers of this fabric the material is capable to attach to the hook fastener attachment means, ATM2 in both sides.
6. To have zones of attachment means such as hook or loop zones of attachment means scattered with a favorable pattern in both sides of the elastic fabric as shown in FIGS. 1-4AB as desired.
6. Any other alteration to make these fabrics more suitable for this use.

The strap means may have holes in its body as shown at FIG. 19 to allow the air and moisture to move. The shiny or the dull surface of the strap means may have zones of attachment means such as loop fastener attachment means, ATM1, hook fastener attachment means, ATM2 and adhesive zones as shown at FIGS. 1, 1A, 2, 3, 3A, 4, 4B, 5, 5A, 6, 6A, 7, 8, 8A, 9 etc. In order to allow further attachment to the support or the body of the strap means, also to parts of the body of the user in order to provide more stability and better function. This property is very important since it will prevent from the strap means to slide and loose its complete function or to cause problem. The strap means may have dots or zones of a sticky material such as latex, rubber or similar in order to prevent two layers of strap means to move and slip an example is shown at FIG. 2A.

Figure 28A:
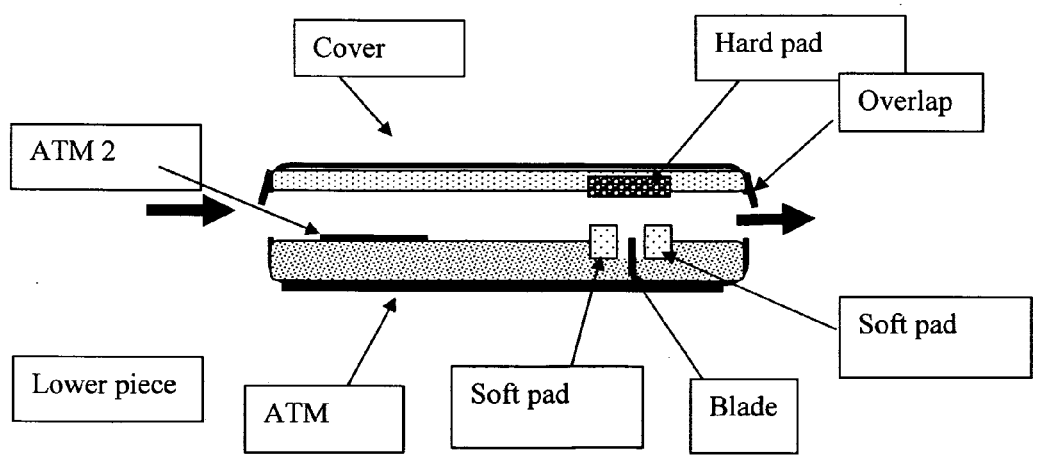

The extra length of strap means may be controlled by an end piece that allows it to be cut at shown at FIGS. 28 and 28A. Also other means such as various attachment means, hooks, etc., may be used for allowing the end piece to be able to fix on the strap after wrapping the limb and coming in contact with its own body. Examples are shown at FIGS. 18, 18A, 19, 20 and 21. D-Rings may be also utilized for allowing the length of the strap means to be controlled and allow an end piece with attachment means to be used with ease. Examples are shown at FIGS. 29, 29A, 29B, 32 and 32A. D-Rings may be also be used for allowing the length of the strap means to be controlled and also to have an adaptor to allow a wide strap to have a small end piece as shown in FIG. 30. A similar unit with a hook at the end is shown at FIG. 31. An adaptor that will allow the length of the strap means to be changed and its end to be controlled and fixed in an adjustable fashion is shown at FIG. 4A. Importantly, the size and shape of the strap means may vary as well as shown at FIGS. 1, 4, 4A, 5, 8, 9, 11, 11A and 24 for reasons such as use in different areas, such as the head, also covering wide areas, such as a limb, allows the strap support means to match the size and shape of a place such as leg etc.

The unit may have more than one strap means as shown at FIGS. 4, 7, 9, 10, 11, 11A ETC., for various reasons such as use in different areas, such as head, covering wide areas, such as a limb, allows the strap support means to match the size and shape of a place such as leg etc.

The use of pad means. The unit may use various pad means as shown in FIGS. 10, 14, 17 and 17A etc., for purposes such as the compression of one area or preventing from compression of one particular area, etc. The pad means may have different sizes, shapes, nature, thickness, stiffness and other important characteristics. The pad means may be made from inflated or inflatable balloons. They may have means of attachment to the support and the straps in order to be placed under the support and over the wound for various means and reasons. Or may have adhesive means to adhere to skin under.

This application also introduces a method of application and the removal of a strap to a limb. This solves the present difficulty with the application and the removal of the straps since the present method used in cases such as the ACE wraps is difficult, time consuming and particularly when the wrap is being unwraped from the limb it turns to be very difficult to wrap it together in an easy fashion for this reason the applicant introduces a hand hold tools shown at FIGS. 22 and 23. These units allows the strap means to be wrapped on the body of this unit and to be applied to the limb easily and at the time of removal from the limb to be re-wrapped on these applicators and to be handled easily. Importantly, these units can be combined with other compression means for further and more complete coverage of the limb or body. Examples of these units is shown at FIGS. 4C and 26. In this method a hose type unit can be worn in areas such as the thigh, knees and/or feet which will combine with these supports so the combination can cover from feet, leg, knee, thigh and lover abdomen area. With chosing different segments of this system the user will be able to use only the feet, ankle-leg area, or the same area with the knee as well and can chose to cover the thigh and the lower abdomen as well. Different combination may be chosen. Importantly, such a hose can be a panty hose that the user can wear from feet to the abdomen area and to have 1. A body that accepts the strap and allows it to be attached to it on a detachable and re-attachable basis.

2. To have zones of attachment means such as ATM2. which will allow a strap means as mentioned in this application to be attached to it on a detachable, re-attachable basis.

Importantly, the application shows a method shown at FIG. 25 which will be very useful in a man made or natural disasters which the time is of extremely significance and can save the lives of many. In this model the envelopes of these units will be attached to the garment of the staff/soldier on a detachable, re-attachable basis. So that the user can grab the unit, pull it hard to detach the unit and use immediately. This process will eliminate the person to search for finding the unit in a bag. Also the person can carry these units which are very light and sturdy in his/her own garment and use it if the need comes.

The application also addresses an issue that is again very important and decisive in man made or natural disasters which the time is of essence and can make a difference in outcome of a victim. For this reason the time should not be vested in any form. To reach this goal the applicant introduces a design shown in FIG. 27. That the package of these units has a line of attachment that allows the cover of this unit to be hold and to be opened in the process of removal of the unit from the attached area of the body of the means that keeps them in place. In this method the attachment of the part of the pocket to the holding unit is strong and allows the pulling to tear the pocket of along a weaker line that is designed.

Explanation of the units with more than one strap. An example of this unit is shown at FIG. 7. In this model a support means, SUP accepts three wide strap means, STR-A, B and C. The strap means are made from stretchable fabric such as Lycra (TM), the free end of the strap has a zone of loop fastener attachment means, ATM1, that will attach to the zones of hook fastener attachment means, ATM2-1 on the support or the ATM2-A, ATM2-A1 AND ATM2-A2 from the initial or the first end of the strap, STR-A on a detachable/re-attachable basis. Importantly, both the outer and inner surfaces of the second end of the strap means shown at ATM1-A has loop fastener attachment means, ATM1. So that it allows both side of end of this strap to be used for this purpose.

The inner/rear surface of the first end of the strap A, STR-A shown in the right side of this strap in this figure which is attached to the support, SUP, has a zone of hook fastener attachment means similar to the ATM2-A which allows this strap to be attached to the support, SUP on a detachable, re-attachable means. Importantly, both, the outer/front and the inner/rear surfaces of this end, ATM2-A will be made from the hook fastener attachment means, ATM2. So that this allows both side of this strap to be used for this purpose.

The second strap, the strap B, STR-B also has similar body except the oblique part of the free end, ATM1-B will vary in order to match the anatomy of the leg of the most of the people, which usually the mid-upper part of the leg is bulged out. The inner end of the strap B, STR-B which also attaches to the support, SUP, has a zone of hook fastener attachment means, similar to the zone of ATM2-B which allows this strap to be attached to the support, SUP on a detachable, re-attachable attachment basis. Importantly, both, the outer/front and the inner/rear surfaces of this end, ATM2-B is made from the hook fastener attachment means, ATM2. So that this allows both side of this strap to be used for this purpose.

The third strap, the strap C, STR-C also has similar to the strap B except the length of this part is shorter. Since it will be placed in the lower part of the leg. It has the free end, ATM1-C and the ATM2-C. The extra zones of the hook fastener attachment means, ATM2-A1 and ATM2-A2 on the front/outer surface of the strap STR-A are designed to allow the end or the body of the strap A, STR-A to be attached to these on a detachable/re-attachable basis. This is important since it allows the end piece to be attached to it and be controlled and also it provides a wider range of the hook fastener attachment means, to be available for the end piece ATM1-B to attach. Thus not only this can be used in a different sizes of the persons but also it allows the level of the tension to be chosen.

This design has many advantages, it allows the straps to be
1. Removed to allow the use of lesser numbers of the straps.
2. To be re-positioned since a given area may need more compression that others.
3. To be designed in different shape.
4. For being washed.
5. For any other purposeful use.
6. To allow the unit to be made with choice, for example a provider can chose a support and in a person with heavy legs to chose the longer straps of proper sizes and attach to the support and in a very short time to make a useful unit. Alternatively, the provider can make a unit for a person with thin legs by chosing the support and a series of the pre-manufactured, shorter straps of proper sizes and attach to the support and have the unit ready for use in a very short period of time.
7. Also Importantly, since the anatomy of the legs of the most of the people, is so that usually the mid-upper part of the leg is bulged out and it has lesser circumstance in the both the upper and the lower part of the legs. The oblique end piece of these straps, allow the end to be attached to the support in a proper line.
8. Importantly, the particular build of these straps allow a strap such as the strap A, STR-A to be rotated 180 degree and to be attached to the lower third of the support, SUP, in order to function as the strap C. STR-C for use in a different patient. This provides significant advantage in having a lesser models of these straps available for making straps in different person.
9. Importantly, this method also allows a number of these straps also to be attached to the other side of the support, SUP in order to allow the straps coming from different directions for a better control of the support.
10. Importantly, this method also allows more numbers of these straps to be attached over the first layer of the straps to make more layers of the straps, in order to cover the limb more and intensify the tension on the limb if needed.
11. Importantly, this method also allows the effective length of these straps to be changed by two ways.
   a. By attaching the attachment site of the strap for example in the case of the strap a, the ATM2-A on the support, SUP. This can be close or reasonably away from the left border of the support, SUP.
   b. By attaching the attachment means on the free end of the strap means for example in the case of the strap A, the ATM1-A on the support, SUP. This can be close or reasonably away from the right border of the support, SUP. By doing so the unit can be adjusted in order to provide comfort to the user, when the condition changes during the use for example the leg is thin at the time when the person leaves the bed from sleeping in a supine position compared to the time that the person has been up during the day time. Thus the adjustability is very valuable.
12. Importantly, further control of the length of the strap means, strap, STR-A, STR-B and STR-C and similar can be achieved by cutting of the strap beyond the outer border of the site of the ATM2-A1 or ATM2-A2. By this method the effective length of the strap can be shortened.
13. Importantly, the attachment of the straps, A, B and C to the end pieces of the ATM1-A, ATM1-B and ATM-C will be done on a detachable, re-attachable basis, by use of a zone of hook fastener attachment means shown at ATM2-AA and ATM2-BB. etc This allows the site and the directions of the attachment area to be adjustable.

This figure also shows that the width of the straps or their shape may vary to satisfy different needs. For example in this model the strap B, STR-B can be wider in order to overlap the other straps, STR-A and STR-C for a better coverage of the limb.

Other important properties of these units are shown in other figures which the applicant has the intention of explaining them in more detail in the regular application.

Importantly, the size, shape, relative sizes, the material and other important characteristics of these units may vary.

What is claimed is:

1. A wrap for compressively wrapping a portion of a living body, the wrap comprising:
   A) a relatively non-stretchable support; and
   B) a relatively stretchable strap i) that has one end portion attached to the support and a free end portion opposite the one end portion, ii) that along at least some of its length comprises relatively stretchable material that is relatively stretchable in a direction lengthwise from the one end portion, and iii) that, with the support disposed against an area of a portion of a living body around which the wrap is being wrapped, has sufficient length that, when stretched, is capable of initially encircling the portion of the living body and detachably/re-attachably attaching to attachment means on the support by direct surface-to-surface attachment of a portion of an inner surface of the relatively stretchable material facing toward the portion of the living body to the attachment means on the support while leaving some additional length of the relatively stretchable material between its detachable/re-attachable attachment to the attachment means on the support and its free end portion,
   wherein the relatively stretchable material forms at least some of the initial encirclement and at least some of the additional stretchable length and has an outer surface that faces away from the portion of the living body and is capable of detachable/re-attachable attachment to an attachment means by direct surface-to-surface attachment, and
   including at least one piece of attachment material on each of the inner and outer surfaces to which the opposite surface detachably/re-attachably attaches by direct surface-to-surface contact.

2. A wrap as set forth in claim 1 in which the outer surface of the relatively stretchable material is not mutually co-extensive with the inner surface of the relatively stretchable material along at least some of the length of the strap.

3. A wrap as set forth in claim 2 in which the strap comprises two lengthwise segments attached end-to-end to one another, each segment comprising a respective piece of relatively stretchable material, one piece of relatively stretchable material having its inner surface capable of detachable/re-attachable attachment to hook-type material by direct surface-to-surface attachment, the other piece of relatively stretchable material having its outer surface capable of detachable/re-attachable attachment to hook-type material by direct surface-to-surface attachment.

4. A wrap as set forth in claim 1 in which at least some of the outer surface of the relatively stretchable material and at least some of the inner surface of the relatively stretchable material are mutually co-extensive along the length of the strap.

5. A wrap as set forth in claim 1 in which the at least one piece of attachment material on each of the inner and outer surfaces to which the opposite surface are detachably/re-attachably attached by direct surface-to-surface contact comprises hook-type attachment material.

6. A wrap for compressively wrapping a portion of a living body, the wrap comprising: A) a relatively non-stretchable support; and B) a relatively stretchable strap i) that has one end portion attached to the support and a free end portion opposite the one end portion, ii) that along at least some of its length comprises relatively stretchable material that is relatively stretchable in a direction lengthwise from the one end portion, and iii) that, with the support disposed against an area of a portion of a living body around which the wrap is being wrapped, has sufficient length that, when stretched, is capable of initially encircling the portion of the living body and detachably/re-attachably attaching to an attachment means on the support by direct surface-to-surface attachment of the relatively stretchable material to the attachment means on the support while leaving some additional length of the relatively stretchable material between its detachable/re-attachable attachment to the attachment means and its free end portion, wherein the relatively stretchable material forms at least a portion of the initial encirclement and at least a portion of the additional stretchable length and has opposite surfaces, namely an inner surface for facing toward the portion of the living body and an outer surface for facing away from the portion of the living body, and further including additional attachment means on a portion of the additional stretchable length for deattachably/re-attachably attaching to the outer surface of the relatively stretchable material in a prior encirclement by direct surface-to-surface contact of the additional attachment means with the relatively stretchable material, wherein the strap comprises two separate straps detachably/re-attachably attached together end-to-end, each separate strap comprising some of the additional attachment means.

7. A wrap as set forth in claim 6 wherein the relatively stretchable material comprises a surface that possesses a loop-type fastener fastening characteristic, each individual strap comprises a respective length of the stretchable material, in one individual strap the surface that possesses a loop-type fastener fastening characteristic forms the outer surface, and in the other individual strap the surface that possesses a loop-type fastener fastening characteristic forms the inner surface.

8. A wrap for compressively wrapping a portion of a living body, the wrap comprising: A) a relatively non-stretchable support; and B) a relatively stretchable strap i) that has one end portion attached to the support and a free end portion opposite the one end portion, ii) that along at least some of its length comprises relatively stretchable material that is relatively stretchable in a direction lengthwise from the one end portion, and iii) that, with the support disposed against an area of a portion of a living body around which the wrap is being wrapped, has sufficient length that, when stretched, is capable of initially encircling the portion of the living body and detachably/re-attachably attaching to an attachment means on the support by direct surface-to-surface attachment of the relatively stretchable material to the attachment means on the support while leaving some additional length of the relatively stretchable material between its detachable/re-attachable attachment to the attachment means and its free end portion, wherein the relatively stretchable material forms at least a portion of the initial encirclement and at least a portion of the additional stretchable length and has opposite surfaces, namely an inner surface for facing toward the portion of the living body and an outer surface for facing away from the portion of the living body, and further including additional attachment means on a portion of the additional stretchable length for deattachably/re-attachably attaching to the outer surface of the relatively stretchable material in a prior encirclement by direct surface-to-surface contact of the additional attachment means with the relatively stretchable material, and an applicator attached to the wrap for applying and/or removing the wrap to compressively wrap and unwrap the wrap to and from a portion of a living body, the applicator comprising,
    a handle that can be grasped, and a mandrel attached to the handle, the mandrel having a zone of attachment means for detachably/re-attachably attaching to the free end portion of the strap so as to allow the strap to be wound on the mandrel prior to applying the wrap, then unwound from the mandrel by manipulating the applicator via the handle to wrap the strap around the portion of the living body during wrapping, and to allow the strap to be rewound on the mandrel during unwrapping.

9. A wrap for compressively wrapping a portion of a living body, the wrap comprising:
  A) a relatively non-stretchable support; and
  B) a relatively stretchable strap i) that has one end portion attached to the support and a free end portion opposite the one end portion, ii) that along at least some of its length comprises relatively stretchable material that is relatively stretchable in a direction lengthwise from the one end portion, and iii) that, with the support disposed against an area of a portion of a living body around which the wrap is being wrapped, has sufficient length that, when stretched, is capable of initially encircling the portion of the living body and detachably/re-attachably attaching to an attachment means on the support by direct surface-to-surface attachment of the relatively stretchable material to the attachment means on the support, to encircle the portion of the living body a second time and detachably/re-attachably attach to the attachment means on the support by direct surface-to-surface attachment of relatively stretchable material to the attachment means on the support while leaving some additional length of the relatively stretchable material for encircling and compressively wrapping the portion of the living body without encircling the support.

* * * * *